United States Patent
Calhoun et al.

(10) Patent No.: US 7,537,782 B2
(45) Date of Patent: May 26, 2009

(54) METHODS FOR GOVERNING BONE GROWTH

(75) Inventors: Christopher J. Calhoun, San Diego, CA (US); G. Bryan Cornwall, San Diego, CA (US)

(73) Assignee: Kensey Nash Corporation, Exton, PA (US)

(*) Notice: Subject to any disclaimer, the term of this patent is extended or adjusted under 35 U.S.C. 154(b) by 1066 days.

(21) Appl. No.: 10/375,451

(22) Filed: Feb. 27, 2003

(65) Prior Publication Data

US 2003/0185874 A1    Oct. 2, 2003

Related U.S. Application Data

(60) Provisional application No. 60/360,462, filed on Feb. 28, 2002, provisional application No. 60/409,103, filed on Sep. 9, 2002.

(51) Int. Cl.
*A61F 2/28* (2006.01)

(52) U.S. Cl. .............. 424/426; 523/112; 523/115; 528/323; 528/324; 528/326; 623/16.11; 623/17.11; 623/23.58

(58) Field of Classification Search .............. 523/115; 514/12
See application file for complete search history.

(56) References Cited

U.S. PATENT DOCUMENTS

| | | | |
|---|---|---|---|
| 5,030,220 A | 7/1991 | Howland | |
| 5,270,300 A * | 12/1993 | Hunziker | 514/12 |
| 5,412,068 A | 5/1995 | Tang et al. | |
| 5,437,672 A | 8/1995 | Alleyne | |
| 5,626,861 A * | 5/1997 | Laurencin et al. | 424/426 |
| 5,679,723 A * | 10/1997 | Cooper et al. | 523/115 |
| 5,795,584 A | 8/1998 | Totakura et al. | |
| 6,005,162 A * | 12/1999 | Constantz | 128/898 |
| 6,034,140 A | 3/2000 | Schwartz et al. | |
| 6,133,325 A | 10/2000 | Schwartz et al. | |
| 6,136,333 A | 10/2000 | Cohn et al. | |
| 6,153,252 A | 11/2000 | Hossainey et al. | |
| 6,331,312 B1 * | 12/2001 | Lee et al. | 424/426 |
| 6,719,795 B1 * | 4/2004 | Cornwall et al. | 623/17.11 |
| 7,074,239 B1 * | 7/2006 | Cornwall et al. | 623/17.11 |

OTHER PUBLICATIONS

Casey K. Lee and Harold Alexander, Prevention of Postlaminectomy Scar Formation, 305-312.

* cited by examiner

*Primary Examiner*—Neil Levy
(74) *Attorney, Agent, or Firm*—Stout, Uxa, Buyan & Mullins, LLP

(57) ABSTRACT

Resorbable polymer barrier membranes and methods of their applications are disclosed. In a broad embodiment, methods of governing bone growth, or preventing bone growth into a certain spatial area, includes the step of forming a spatial barrier with the present resorbable barrier membrane. The barrier membrane separates a bone-growth area and a non-bone-growth area, and prevents bone from growing into the non-growth area.

59 Claims, 14 Drawing Sheets

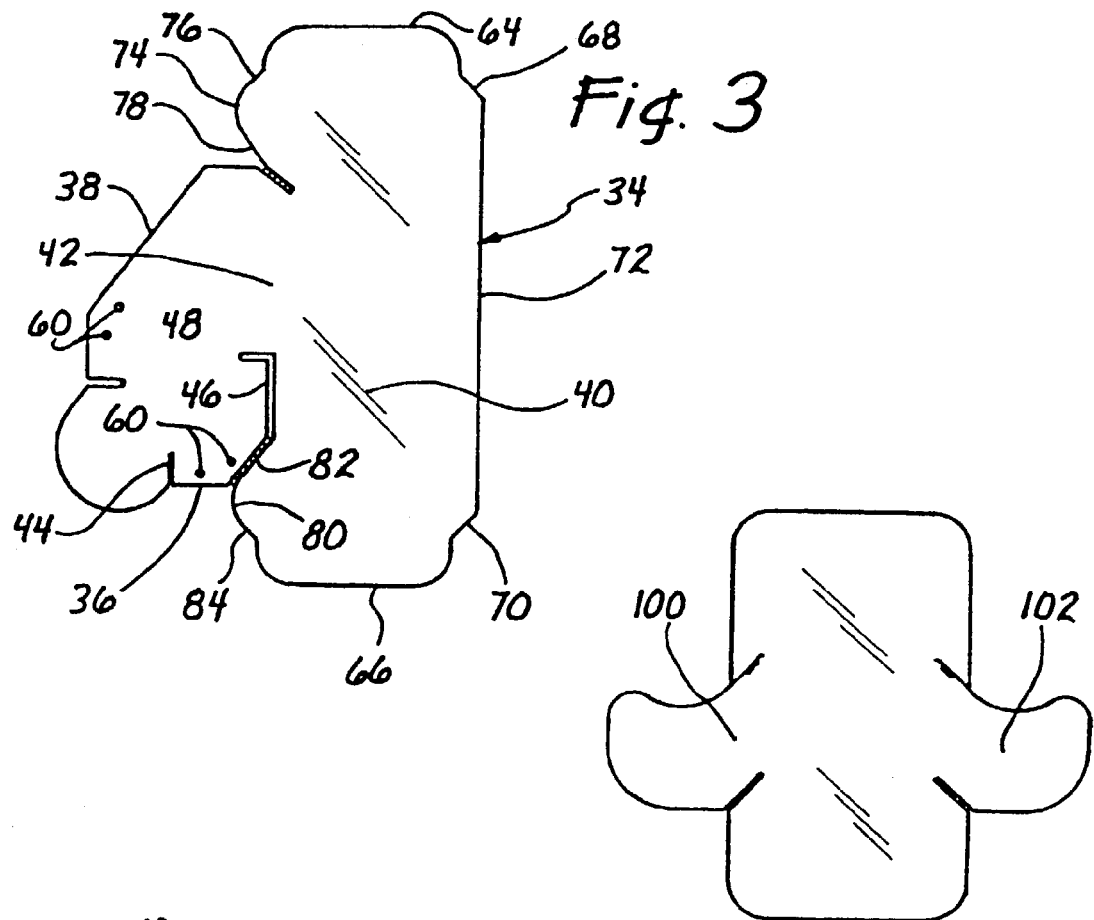
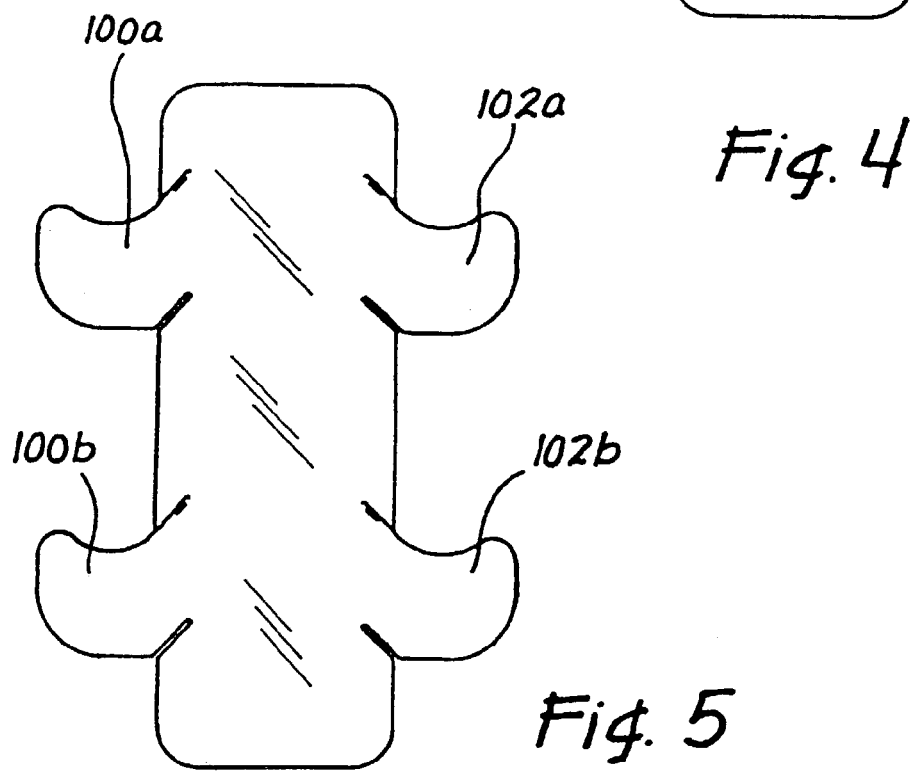

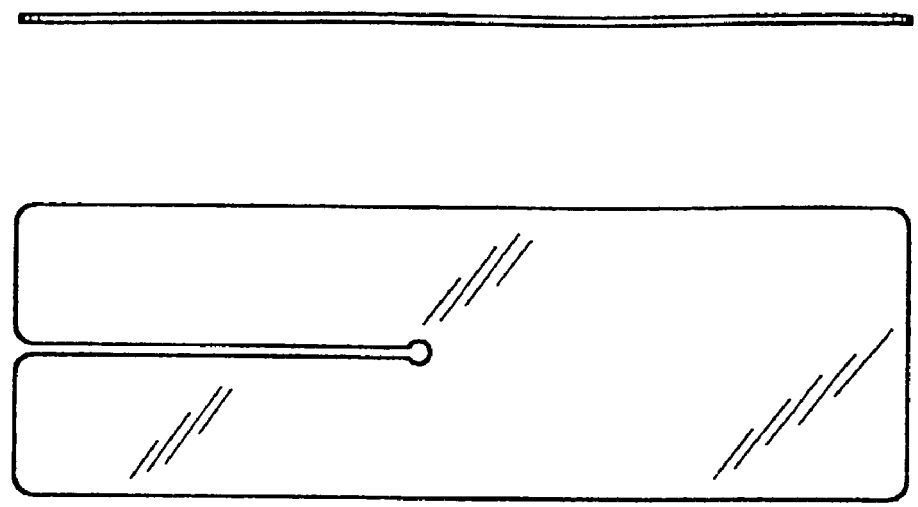
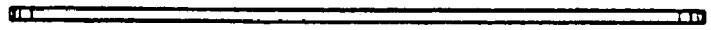
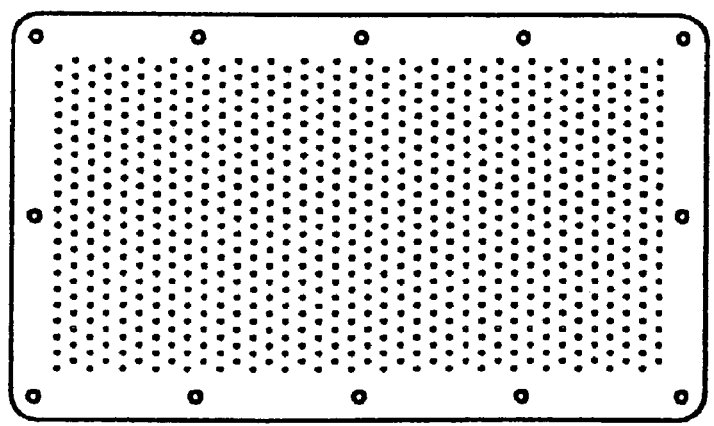
Fig. 7b
Fig. 7a
Fig. 6b
Fig. 6a

Fig. 15a
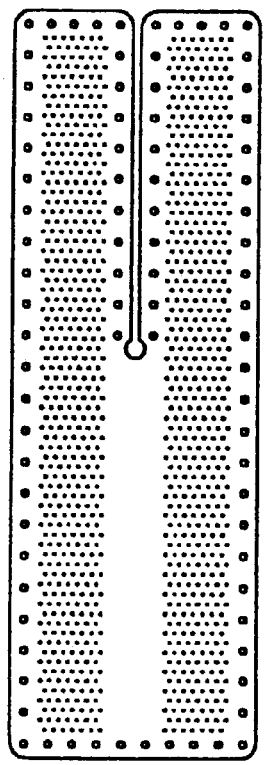
Fig. 15b
Fig. 16a
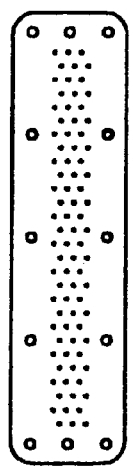
Fig. 16b

METHODS FOR GOVERNING BONE GROWTH

CROSS-REFERENCE TO RELATED APPLICATIONS

This application claims the benefit of U.S. Application No. 60/360,462, entitled METHODS FOR GOVERNING BONE GROWTH, and filed Feb. 28, 2002, and U.S. Application No. 60/409,103, entitled METHODS FOR GOVERNING BONE GROWTH, and filed Sep. 9, 2002, the entire contents of which are hereby incorporated by reference.

BACKGROUND OF THE INVENTION

1. Field of the Invention

The present invention relates generally to medical devices and, more particularly, to methods for governing bone growth.

2. Description of Related Art

A plethora of conditions fall under the general characterization of having a need to enhance bone formation or bone growth. These conditions include bone segmental defects, periodontal disease, metastatic bone disease, osteolytic bone disease and conditions where connective tissue repair would be beneficial, such as healing or regeneration of cartilage defects or injury. One particular condition characterized by a need to enhance bone growth is spinal disk injury.

Various bone inductive factors have been employed to stimulate bone growth. For example, bone morphological proteins (BMPs) are novel factors in the extended transforming growth factor beta superfamily. They were first identified by Wozney J. et al. Science (1988) 242:1528-34, using gene cloning techniques, following earlier descriptions characterizing the biological activity in extracts of demineralized bone (Urist M. Science (1965) 150:893-99). Recombinant BMP2 and BMP4 can induce new bone growth when they are injected locally into the subcutaneous tissues of rats (Wozney J. Molec Reprod Dev (1992) 32:160-67). These factors are expressed by normal osteoblasts as they differentiate, and have been shown to stimulate osteoblast differentiation and bone nodule formation in vitro as well as bone formation in vivo (Harris S. et al. J. Bone Miner Res (1994) 9:855-63).

Bone inductive factors are useful in that they can facilitate bone growth to treat a condition. However, ungoverned bone growth triggered by such bone inductive factors can also be problematic.

For example, an effective method of treating spinal disk injury is a discectomy, or surgical removal of a portion or all of an intervertebral disc followed by fusion of the adjacent vertebrae. The fusion is often accomplished by locking the adjacent vertebrae together with a spinal cage, and administering a bone inductive factor (e.g., BMP) in between the vertebrae to facilitate bone growth and fusion of the adjacent vertebrae. However, the administered bone inductive factor may cause bone growth in the spinal canal, which in turn may cause additional problems including increased intraspinal pressure and pinched nerves.

Such problems may be attenuated or eliminated with a method for governing bone growth, and directing the growth away from undesirous areas, such as areas within the spinal canal. Thus, there is a need for improved methods of governing bone growth.

SUMMARY OF THE INVENTION

The present invention addresses these needs by providing resorbable polymer bone growth barrier membranes. The invention herein discloses bone growth barrier membranes, which are engineered to be absorbed into the body relatively slowly over time in order to reduce potential negative side effects, and methods of governing, attenuating or eliminating an occurrence of bone growth into undesirous areas. The bone growth barrier membranes can be formed to have thicknesses on the order of microns, such as, for example, thicknesses between 10 and 300 microns. The barrier membranes can be preshaped with welding flanges and stored in sterile packaging. In one embodiment, a method of governing bone growth is featured.

Any feature or combination of features described herein are included within the scope of the present invention provided that the features included in any such combination are not mutually inconsistent as will be apparent from the context, this specification, and the knowledge of one of ordinary skill in the art. Additional advantages and aspects of the present invention are apparent in the following detailed description and claims.

BRIEF DESCRIPTION OF THE DRAWINGS

FIG. 1b is a cross sectional view of the vertebrae in FIG. 1a;

FIG. 3 illustrates a scar-reduction resorbable barrier membrane for application to the exiting nerve root of the spinal chord in accordance with a first pre-formed embodiment of the present invention;

FIG. 4 illustrates a scar-reduction resorbable barrier membrane for application to two exiting nerve roots of the spinal chord in accordance with a second pre-formed embodiment of the present invention;

FIG. 5 illustrates a scar-reduction resorbable barrier membrane for application to four exiting nerve roots of the spinal chord in accordance with a third pre-formed embodiment of the present invention;

FIG. 6a is a top planar view of a scar-reduction resorbable barrier membrane in accordance with a fourth pre-formed embodiment of the present invention;

FIG. 6b is a cross-sectional view of the scar-reduction resorbable barrier membrane shown in FIG. 6a;

FIG. 7a is a top planar view of a scar-reduction resorbable barrier membrane in accordance with a fifth pre-formed embodiment of the present invention;

FIG. 7b is a cross-sectional view of the scar-reduction resorbable barrier membrane shown in FIG. 7a;

FIG. 8b is a cross-sectional view of the scar-reduction resorbable barrier membrane shown in FIG. 8a;

FIG. 9a is a top planar view of a scar-reduction resorbable barrier membrane in accordance with a seventh pre-formed embodiment of the present invention;

FIG. 9b is a cross-sectional view of the scar-reduction resorbable barrier membrane shown in FIG. 9a;

FIG. 10b is a cross-sectional view of the scar-reduction resorbable barrier membrane shown in FIG. 10a;

FIG. 11b is a cross-sectional view of the scar-reduction resorbable barrier membrane shown in FIG. 11a;

FIG. 12a is a top planar view of a scar-reduction resorbable barrier membrane in accordance with a tenth pre-formed embodiment of the present invention;

FIG. 12b is a cross-sectional view of the scar-reduction resorbable barrier membrane shown in FIG. 12a;

FIG. 13b is a cross-sectional view of the scar-reduction resorbable barrier membrane shown in FIG. 13a;

FIG. 14b is a cross-sectional view of the scar-reduction resorbable barrier membrane shown in FIG. 14a;

FIG. 15a is a top planar view of a scar-reduction resorbable barrier membrane in accordance with a thirteenth pre-formed embodiment of the present invention;

FIG. 15b is a cross-sectional view of the scar-reduction resorbable barrier membrane shown in FIG. 15a;

FIG. 16a is a top planar view of a scar-reduction resorbable barrier membrane in accordance with a fourteenth pre-formed embodiment of the present invention;

FIG. 16b is a cross-sectional view of the scar-reduction resorbable barrier membrane shown in FIG. 16a;

FIG. 17a is a top planar view of a scar-reduction resorbable barrier membrane in accordance with a fifteenth pre-formed embodiment of the present invention; and FIG. 17b is a cross-sectional view of the scar-reduction resorbable barrier membrane shown in FIG. 17a.

DESCRIPTION OF THE PRESENTLY PREFERRED EMBODIMENTS

Figure 1A:
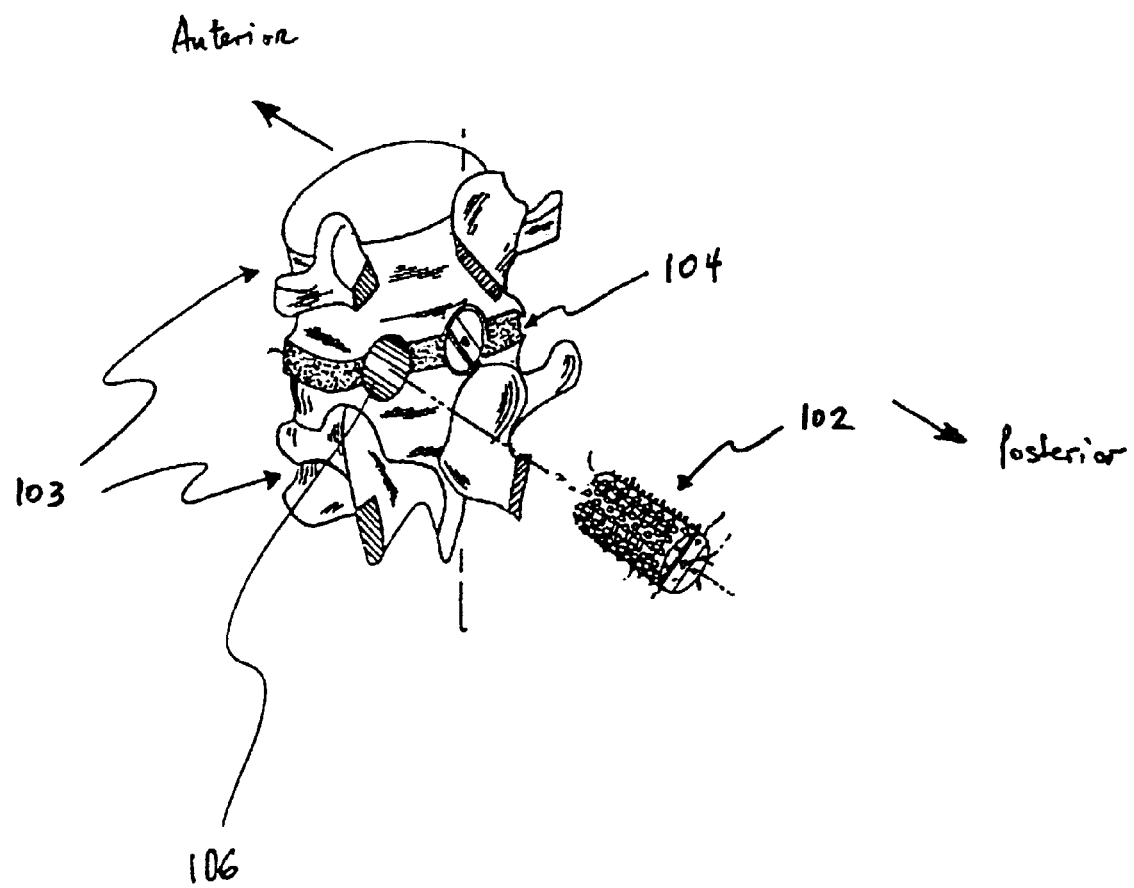
FIG. 1a illustrates the fusion process of two vertebrae using a spinal cage and a construction for preventing bone growth into the spinal canal.

Reference will now be made in detail to the presently preferred embodiments of the invention, examples of which are illustrated in the accompanying drawings. Wherever possible, the same or similar reference numbers are used in the drawings and the description to refer to the same or like parts. It should be noted that the drawings are in simplified form and are not to precise scale. In reference to the disclosure herein, for purposes of convenience and clarity only, directional terms, such as, top, bottom, left, right, up, down, over, above, below, beneath, rear, and front, are used with respect to the accompanying drawings. Such directional terms should not be construed to limit the scope of the invention in any manner.

Although the disclosure herein refers to certain illustrated embodiments, it is to be understood that these embodiments are presented by way of example and not by way of limitation. The intent of the following detailed description is to cover all modifications, alternatives, and equivalents as may fall within the spirit and scope of the invention as defined by the appended claims.

The present invention provides a resorbable implant in barrier membrane form that can be used in various surgical contexts, including applications wherein the barrier membrane is implemented to prevent bone growth into undesirous areas, such as the spinal canal or cartilage.

In a broad embodiment, methods of governing bone growth, or attenuating or eliminating an occurrence of bone growth, within a certain spatial area, comprise steps of forming a spatial barrier with the resorbable barrier membrane of the present invention. The barrier membrane separates a bone-growth area from a limited or non-bone-growth area. The bone-growth area is defined to be the spatial area where it is desirous for bone to grow.

In accordance with one aspect of the present invention, bone growth in the bone-growth area may be stimulated with a bone inductive factor, such as a BMP. The non-bone-growth area is defined to be the spatial area where it is desirous for bone to grow at an attenuated rate or not at all. The non-bone-growth area can be substantially free of a bone inductive factor. In one embodiment, the non-bone-growth area may further be filled with anti-tissue agents, such as anti-bone agents. In accordance with another embodiment, the barrier membrane governs bone growth and allows bone to grow at a governed rate only within the bone-growth area and not beyond. For example, bone does not grow through or beyond the physical borders defined by the barrier membrane of the present invention or, in another embodiment, grows through the barrier membrane at a controlled reduced rate.

In a preferred embodiment of the present invention, methods of governing bone growth in spinal injury treatments are implemented. Spinal injury repair can be achieved by the fusing together of two adjacent vertebrae. Details regarding typical implementations of spinal cages for fusing vertebra are disclosed in U.S. Pat. Nos. 6,033,438 and 5,015,247, the contents of which are incorporated in their entireties herein by reference.

Figure 1B:
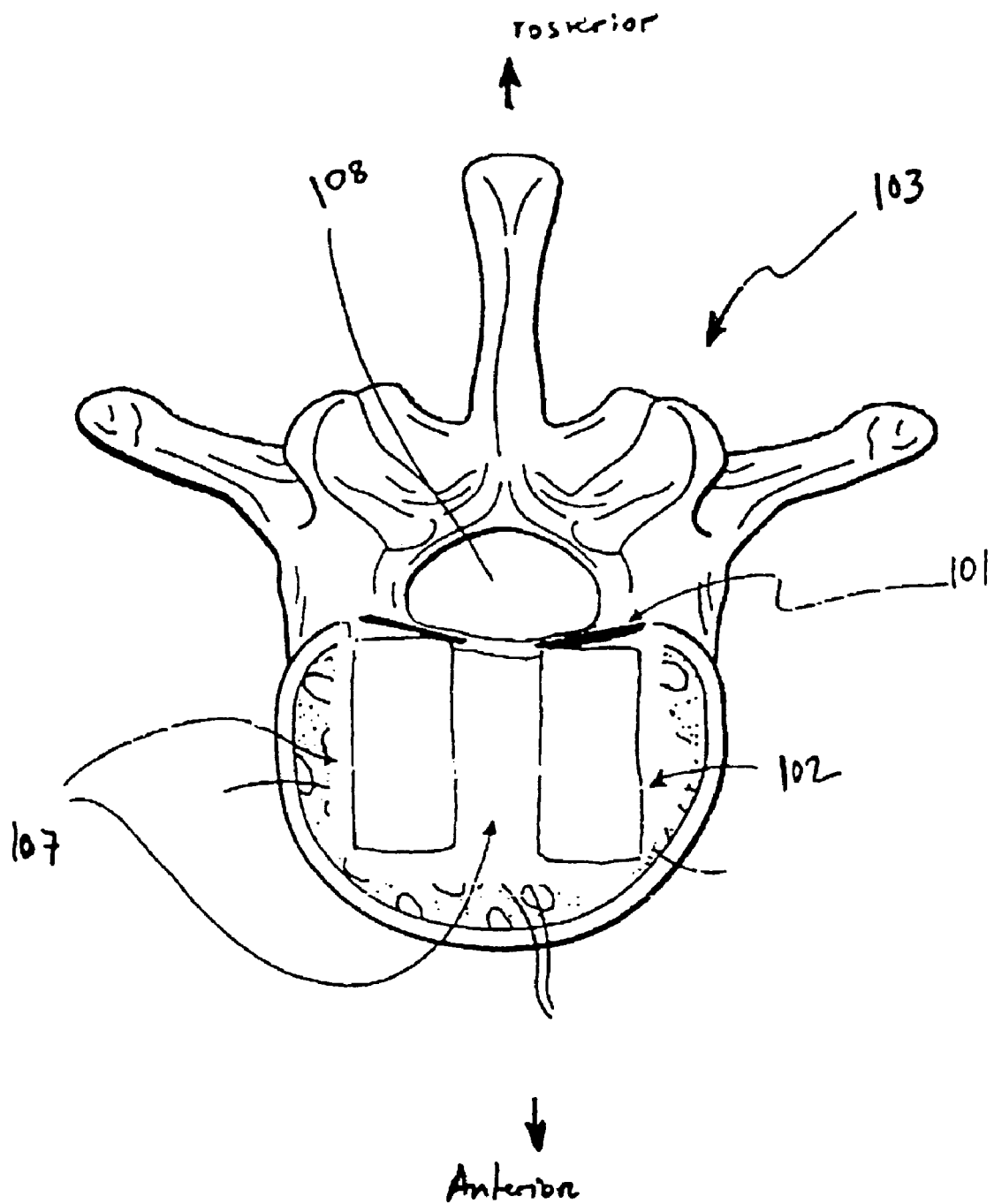

As illustrated in FIGS. 1a and 1b, spinal fusion can be accomplished by forming one or more cavities 106 through the disk 104 and between the vertebrae 103 to be fused. Thereafter, one or more spinal cages 102 are inserted into the one or more cavities 106. Bone inductive factor can be administered into the cavity 106, either directly or indirectly through the spinal cage 102, to induce bone growth and fusion between the vertebrae. A concern with these repair processes is that bone may grow into the spinal canal 108 and result in undesirable side effects.

In accordance with the present invention, a method for governing bone growth, or preventing bone growth, comprises a step of inserting at least one barrier membrane 101 of the present invention into a cavity in a bone. The cavity may be surgically created, or may have resulted from disease or injury. In one example, a method of governing bone growth in a spinal canal 108 comprises a step of lining a surface proximal to the spinal canal 108 with at least one barrier membrane 101 of the present invention. For example, the barrier membrane 101 may be placed adjacent to, or within, the spinal meninges. The spatial area to be lined with the barrier membrane may be engineered to predetermined extents and distributions in order to generate the desired barrier action. In one embodiment, the spatial area over which the barrier membrane is formed is effective to prevent any bone from growing into the cavity in the bone, or into the spinal canal.

The barrier membrane disclosed herein may be impregnated with a tissue growth inhibitor, such as an anti-bone factor. Anti-bone factors for selectively inhibiting bone tissue growth include anti-angiogenic factors, and monoclonal or polyclonal antibodies, including antibody fragments such as Fab', F(ab)$_2$, Fabc, and Fv fragments, or combinations thereof, which are effective against members of the transforming growth factor (TGF)-beta superfamily. Thus, with reference to FIG. 1b, the barrier membrane 101 may be positioned to shield the spinal canal 108 from the bone inductive factors used in connection with the spinal cages 102, to thereby attenuate or eliminate any formation of bone within the spinal canal 108.

The barrier membrane can be attached to an anatomical structure so as to firmly define a fixed border between the bone-growth area and the non-bone-growth area. Various means for attaching the barrier membrane to structures such as muscular tissue, other soft tissue, or bone may be used. For example, sutures or staples may be used to attach the barrier membrane to the paravertebral muscle. As another example, the bridging barrier membrane in particular may be secured to the vertebrae bone using resorbable bone screws or tacks. Tucking or folding the barrier membrane material into anatomical crevices may be sufficient in certain implementations to fix its position. An adhesive such as a fibrin sealant, or a resorbable cyanoacrylate adhesive may further be utilized to secure the barrier membrane, alone or in combination with the above means of attachment. In a presently preferred embodiment, the barrier membrane is heat bonded, such as with a bipolar electro-cautery device, ultrasonically welded, or similarly sealed, as discussed below, directly to the hard and/or soft tissue to which it is to be secured.

The methods of governing bone growth disclosed herein are applicable in full-thickness defect treatments. Full-thickness defects of an articular surface include damage to the hyaline cartilage, the calcified cartilage layer and the subchondral bone tissue with its blood vessels and bone marrow. Full-thickness defects can cause severe pain, since for example the bone plate contains sensory nerve endings. Such defects generally arise from severe trauma or during the late stages of degenerative joint disease, such as osteoarthritis. Full-thickness defects may, on occasion, lead to bleeding and the induction of a repair reaction from the subchondral bone, as discussed in the article "Articular Cartilage: Composition, Structure, Response to Injury, and Methods of Facilitating Repair," in Articular Cartilage and Knee Joint Function: Basic Science and Arthroscopy (New York: Raven Press, 1990) pp. 19-56, by Buckwalter et al. In the case of full-thickness defects, the non-bone-growth area is the cartilage, and a method is provided according to the present invention for preventing bone growth into cartilage tissues after a full-thickness defect treatment.

In general, the repair of full-thickness defects in joints involves filling the defect in the bone portion of a full-thickness defect up to the level of the bone-cartilage interface with a first matrix which will be incorporated into the animal tissue and which is generally biodegradable. See, for example, U.S. Pat. No. 5,270,300, the disclosure of which is incorporated in its entirety herein by reference. The first matrix can contain, for example, angiogenic and osteogenic factors.

According to one aspect of the present invention, the first matrix filling the bone defect can then be covered with a barrier membrane which is impermeable to cells. One purpose of the barrier membrane is to prevent blood vessels from infiltrating into the layer of cartilage in the case of a full-thickness defect, to thereby prevent bone from growing into the cartilage. For instance, the formation of blood vessels in the cartilage can stimulate bone growth in the cartilage and inhibit complete repair of the cartilage layer. The barrier membrane of the present invention can be sealed to the edges of the defect at the cartilage-bone junction, e.g., by sealing to the cartilage by thermal bonding using a thermal knife or laser.

The remaining cartilage portion of the defect can be filled to the top of the cartilage surface with a second matrix, which contains a chondrogenic composition and which will be metabolized or incorporated into the animal tissue (e.g., a biodegradable matrix). The first matrix containing angiogenic and osteogenic factors may also be applied to other bone defects to promote repair. In one embodiment, use of the methods of this invention promote the healing of traumatic lesions and forms of osteoarthritis, which could otherwise lead to loss of effective joint function and ultimate resection and replacement of the joint.

In a broad embodiment, the barrier membranes of the present invention may be constructed from any material effective to govern bone growth, when used in accordance with the methods disclosed herein. Preferably, the barrier membranes are resorbable. For example, barrier membranes of the present invention may be constructed from any biodegradable materials, such as resorbable polymers. In preferred embodiments, the barrier membranes are formed of materials that are not bioreactive, or in other words, do not induce a significant antigenic or immunogenic biological response. Membranes of the present invention may be constructed from various biodegradable materials, such as resorbable polymers. In accordance with one embodiment, non-limiting polymers which may be used to form membranes of the present invention include polymers (e.g., copolymers) of lactide (L, D, DL, or combinations thereof), glycolide, trimethylene carbonate, caprolactone and/or physical and chemical combinations thereof. In one embodiment, the membranes comprise a polylactide, which can be a copolymer of L-lactide and D,L-lactide. For example, the copolymer can comprise about 60-80% of L-lactide and about 20-40% of D,L-lactide, and in a preferred embodiment the copolymer comprises poly (L-lactide-co-D,L-lactide) 70:30 Resomer LR708 manufactured and supplied from Boehringer Ingelheim KG of Germany. Membranes constructed from this material have been found to retard or prevent tissue adhesions, reduce scarring and/or inflammation, and to be resorbable within 24 months or less of implantation into the mammalian body.

In one embodiment, the membranes are formed by polymers (e.g., homo and/or copolymers) derived from one or more cyclic esters, such as lactide (i.e., L, D, DL, or combinations thereof), epsilon-caprolactone and glycolide. For instance, the membranes in one embodiment can comprise about 1 to 99% epsilon-caprolactone, or in another embodiment can comprise 20 to 40% epsilon-caprolactone. In one example, a membrane comprises 65:35 poly (L-lactide-co-epsilon-caprolactone). In other embodiments, butyrolactone, valerolactone, or dimethyl propiolactone can be used with or as a substitute for epsilon-caprolactone. In another embodiment, the membranes can comprise a copolymer including lactide and glycolide which is resorbed into the body more rapidly than the above-mentioned poly (L-lactide-co-D,L-lactide).

The polymers (e.g., co-polymers) of the present invention require relatively simple chemical reactions and formulations. The resorbable barrier membrane of the present invention is preferably smooth and non-porous. Moreover, the barrier membrane is preferably bioabsorbable in the body. A pre-formed barrier membrane made from poly (L-lactide-co- D,L lactide) can be shaped at the time of surgery by bringing the material to its glass transition temperature, using heating iron, hot air, heated sponge or hot water bath methods. The bone-governing barrier membrane of the present invention preferably has a uniform thickness of less than about 300 microns, preferably less than 200 microns, and more preferably between 10 microns and 100 microns. As defined herein, the "barrier membranes" of the present invention comprise thicknesses between 10 microns and 300 microns and, preferably, between 10 and 100 microns.

In one embodiment, the barrier membrane comprises two opposing surfaces. On one side of the barrier membrane, there is a bone-growing substantially-smooth side or surface, and on the other side there is a non-bone growing substantially-smooth side or surface. Preferably, the bone-growing substantially-smooth side is positioned to face the bone-growth area, and the non-bone growing substantially-smooth side is positioned to face the non-bone growth area when placed in a patient. According to another aspect of the invention the barrier membrane comprises a substantially planar barrier membrane of resorbable polymer base material having a single layer of resorbable polymer base marerial desposed between the bone-growing side and the non-bone growing side, and in accordance with other aspects the barrier membrane can comprise a planar barrier membrane, or a substantially planar membrane, of resorbable polymer base material, as elucidated, for example, in FIGS. 6-17.

In one embodiment, the barrier membrane may be provided in any shape which may effectively serve as a barrier to bone growth. In one embodiment, the barrier membrane material may be provided in rectangular shapes that are, for example, several centimeters on each side (length or width), or can be cut and formed into specific shapes, configurations and sizes by the manufacturer before packaging and sterilization. The thin barrier membranes of the present invention are sufficiently flexible to conform around anatomical structures, although some heating in a hot water bath may be desirable for thicker configurations. In modified embodiments, certain poly lactides which become somewhat more rigid and brittle at thicknesses above 0.25 mm and which can be softened by formation with other copolymers and/or other monomers, e.g., epsilon-caprolactone, for example, may be implemented to form bone-governing resorbable barrier micro-barrier membranes. Moreover, in accordance with another aspect of the present invention, the barrier membrane may comprise a substance for cellular control, such as at least one of a chemotactic substance for influencing cell-migration, an inhibitory substance for influencing cell-migration, a mitogenic growth factor for influencing cell proliferation, a growth factor for influencing cell differentiation, and factors which promote angiogenesis (formation of new blood vessels). Preferably, the barrier membranes are impregnated with anti-tissue agents, for example anti-bone agents. Cellular control substances may be located at one or more predetermined locations on the thin-sheet barrier membranes. For example, substances that generally inhibit or otherwise reduce cellular growth and/or differentiation may be located on one surface of the barrier membrane (e.g., the surface that will be in proximity to the non-bone growth area). Similarly, substances that generally promote or otherwise enhance cellular growth and/or differentiation may be located on one surface of the barrier membrane (e.g., the surface that will be in proximity to the bone growth area). Additionally, the inhibiting and promoting substances may be interspersed through the membrane at predetermined locations in the membrane to help influence rates of cellular growth at different regions over the surface of the barrier membranes.

The very thin construction of these barrier membranes is believed to substantially accelerate the rate of absorption of the implants, compared to rates of absorption of thicker barrier membrane implants of the same material. It is believed, however, that resorption into the body too quickly of the barrier membrane will yield undesirable drops in local pH levels, thus introducing/elevating, for example, local inflammation, discomfort and/or foreign antibody responses. Further, a resulting uneven (e.g., cracked, broken, roughened or flaked) surface of a barrier membrane degrading too early may undesirably cause tissue turbulence between the tissues before, for example, adequate healing has occurred, resulting in potential tissue inflammation and scarring. It is believed that a barrier membrane of the present invention having a thickness of about 200 microns or less should maintain its structural integrity for a period in excess of three weeks and, more preferably for at least 7 weeks, before substantially degrading, so that the anti-scarring function can be achieved and optimized. To the extent the barrier membrane does not degrade at an accelerated rate, compared to a thicker barrier membrane of the same material, the barrier membrane should maintain its structural integrity for a period in excess of 6 months and, more preferably for at least one year, before substantially degrading, in order to achieve and optimize the anti-scarring function. The resorbable polymer barrier membranes in accordance with this aspect of the present invention are thus designed to resorb into the body at a relatively slow rate or rates. The rates of resorption of the barrier membranes may also be selectively controlled. For example, the barrier membranes may be manufactured to degrade at different rates depending on the rate of recovery of the patient from a surgical procedure. Thus, a patient who recovers more quickly from a surgical procedure relative to an average patient, may be administered an agent that for example is selective for the polymeric material of the barrier membrane and causes the barrier membrane to degrade more quickly. Or, if the polymeric material is, for example, temperature sensitive or is influenced by electrical charge, the area in which the barrier membrane has been implanted may be locally heated or cooled, or otherwise exposed to an electrical charge that causes the membrane to dissolve at a desired rate for the individual patient.

As used herein, the term "non-porous" refers to a material which is generally water tight and, in accordance with a preferred embodiment, not fluid permeable. However, in a modified embodiment of the invention micro-pores (i.e., fluid permeable but not cell permeable) may exist in the resorbable barrier membrane of the present invention, to the extent, for example, that they do not substantially disrupt the smoothness of the surfaces of the resorbable barrier membrane to cause scarring of tissue. In substantially modified embodiments for limited applications, pores which are cell permeable but not vessel permeable may be manufactured and used. As presently preferred, the resorbable barrier membrane is manufactured using a press molding procedure to yield a substantially non-porous film. The barrier membrane materials of present invention may have a semi-rigid construction, and are fully contourable when heated to approximately 55 degrees Celsius. As presently embodied, many of the thinner barrier membrane thicknesses can be sufficiently contoured even in the absence of heating.

The non-porosity and the smoothness of the barrier membrane can reduce tissue turbulence, enhance tissue guidance, and minimize scar formation. Moreover, the smooth, uninterrupted surface of the barrier membrane material may facilitate movement of the dura and local tissues across the area, hence reducing frictional rubbing and wearing which may induce scar tissue formation.

The material may be used in a number of other surgical applications, including: surgical repair of fracture orbital floors, surgical repair of the nasal septum and perforated ear drum barrier membrane, as a protective sheathing to facilitate osteogenesis, surgical repair of the urethral anatomy and repair of urethral strictures, prevention of synostosis in completed corrective surgery for cranial fusions and forearm fractures, lessening of soft-tissue fibrosis or bony growth, as a temporary covering for prenatal rupture omphalocele during staged repair procedures, guided tissue regeneration between the teeth and gingival margin, tympanic barrier membrane repairs, dural coverings and neural repair, heart vessel repair, hernia repair, tendon anastomoses, temporary joint spacers, wound dressings, scar coverings, and as a covering for gastroschisis.

In one embodiment, the barrier membranes are also effective as a scar-tissue reduction membrane and/or to prevent tissue adhesions. As such, the barrier membrane maybe referred to as a scar-reduction resorbable barrier membrane. In one embodiment, the barrier membranes are also effective as an anti-tissue adhesion membrane. In one embodiment, the barrier membrane material of the present invention is particularly suitable for preventing tissue from abnormally fibrotically joining together following surgery, which can lead to abnormal scarring and interfere with normal physiological functioning. In some cases, such scarring can force and/or interfere with follow-up, corrective, or other surgical operations.

For example, there is evidence pointing to epidural adhesions as possible factors contributing to failed back surgery. Epidural fibrosis may occur following spinal injuries or as a post-operative surgical complication. The dense scar formation on dura and around nerve roots has previously been described as the "laminotomy barrier membrane," and has been implicated in rendering subsequent spine operations technically more difficult. In a laminectomy procedure, for example, the scar-reduction resorbable barrier membrane of the present invention is desirably inserted between the dural sleeve and the paravertebral musculature post laminotomy and conforms readily to block exposed marrow elements of the laminae. Imposition of the barrier membrane material as a barrier between the paravertebral musculature and the epidural space is believed to reduce cellular trafficking and vascular invasion into the epidural space from the overlying muscle and adjacent exposed cancellous bone. Moreover, tests have shown that the present barrier membrane material does not appear to interfere with normal posterior wound healing while at the same time inhibiting the unwanted adhesions and scarring.

Figure 2A:
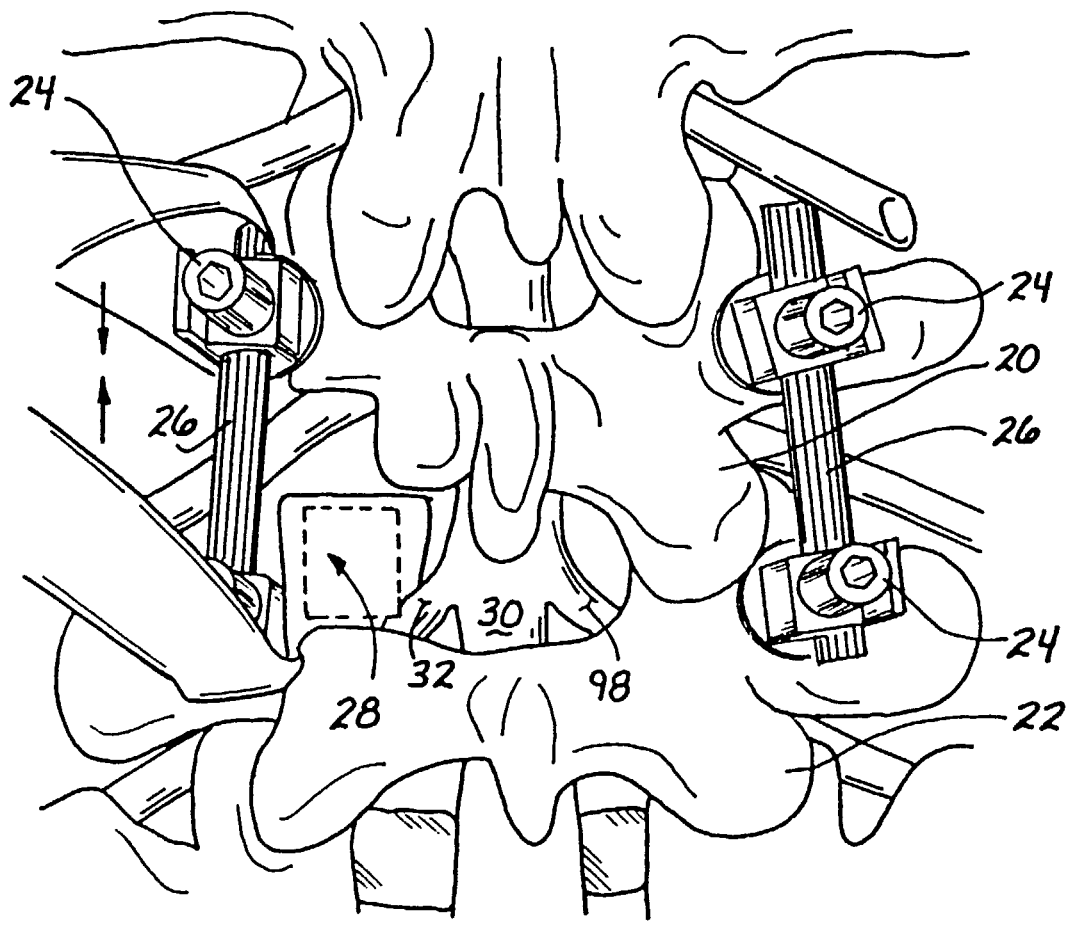
FIG. 2a illustrates a laminotomy procedure wherein a portion of the posterior arch (lamina) of a vertebra is surgically removed.
Figure 2B:
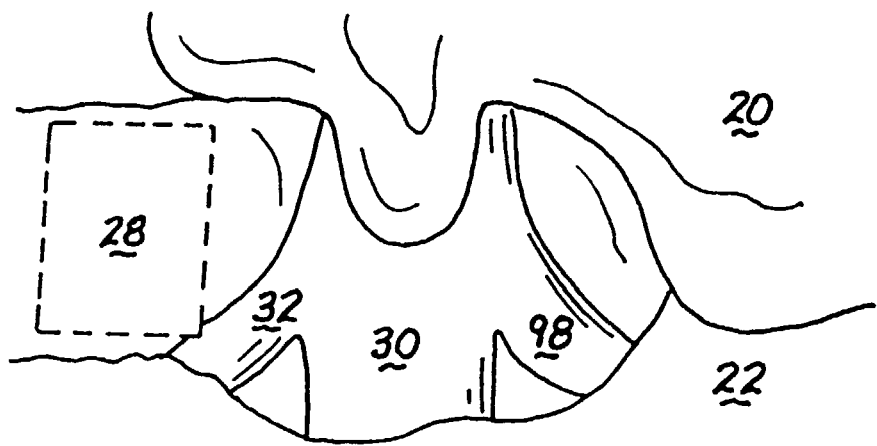
FIG. 2b is an enlarged view of FIG. 2A.
Figure 8B:
Figure 8A:
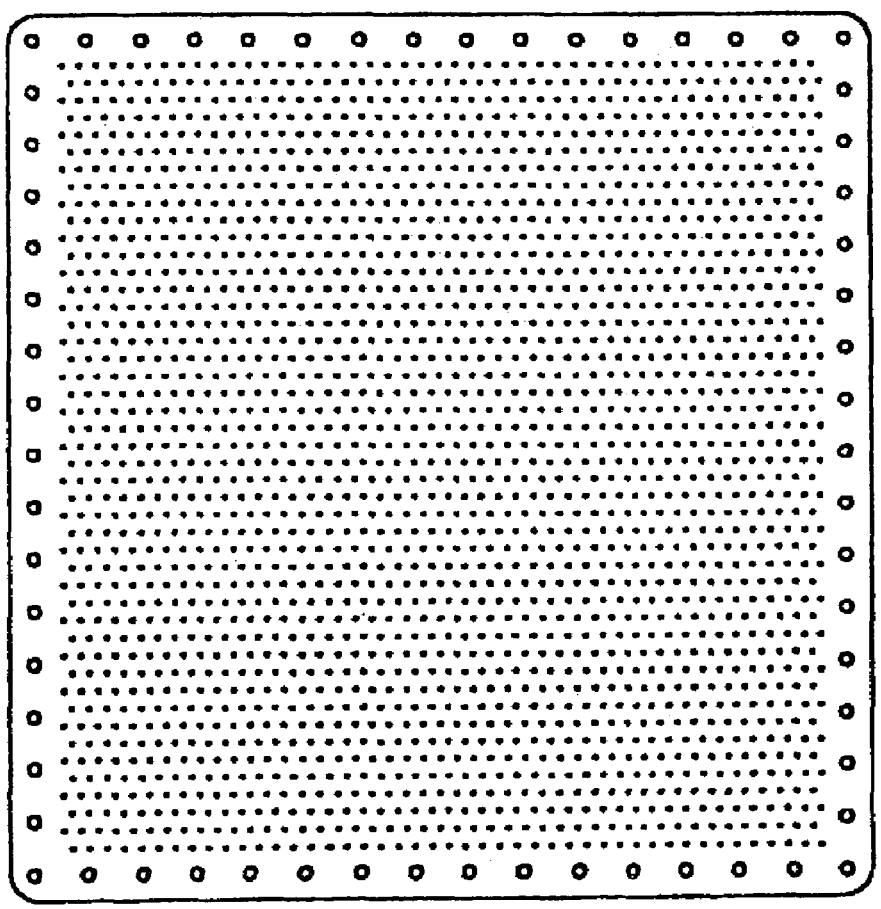
FIG. 8a is a top planar view of a scar-reduction resorbable barrier membrane in accordance with a sixth pre-formed embodiment of the present invention.
Figures 9A, 9B:
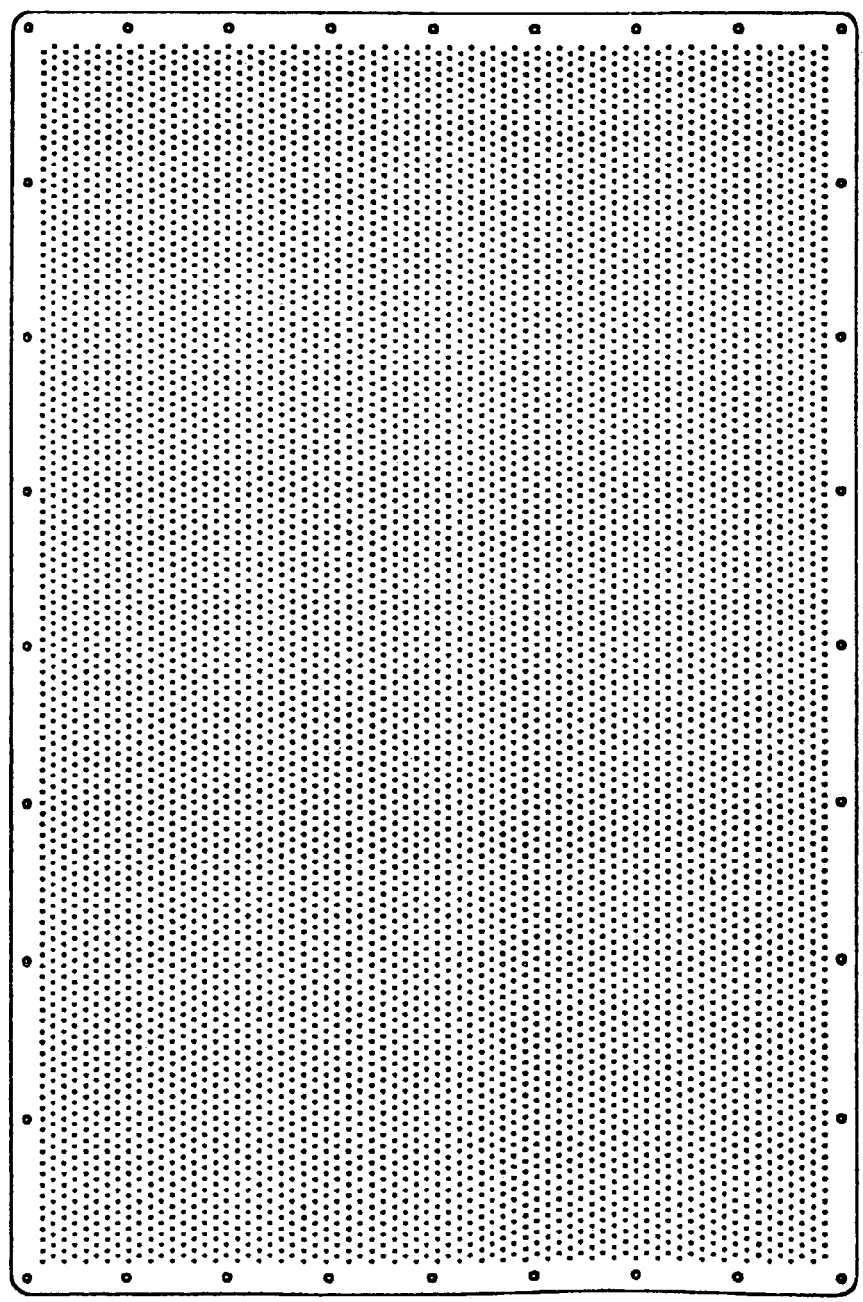
Figure 10A:
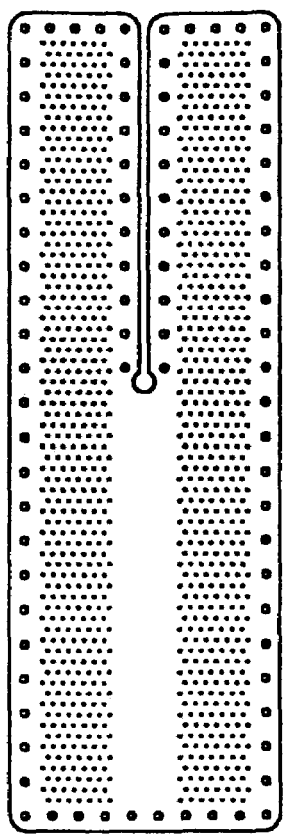
FIG. 10a is a top planar view of a scar-reduction resorbable barrier membrane in accordance with an eighth pre-formed embodiment of the present invention.
Figure 10B:
Figure 11A:
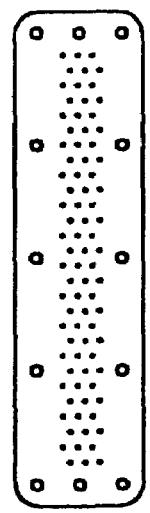
FIG. 11a is a top planar view of a scar-reduction resorbable barrier membrane in accordance with a ninth pre-formed embodiment of the present invention.
Figure 11B:
Figures 12A, 12B:
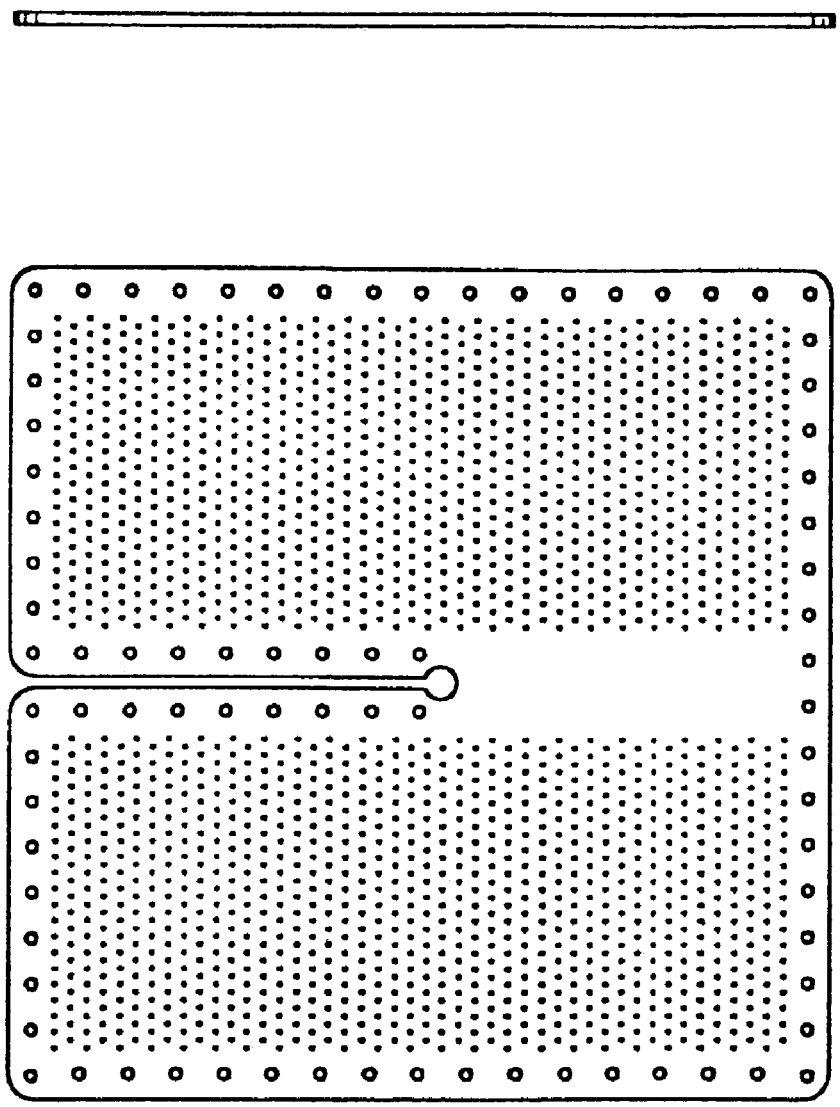
Figure 13A:
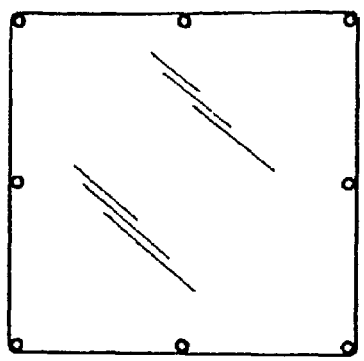
FIG. 13a is a top planar view of a scar-reduction resorbable barrier membrane in accordance with an eleventh pre-formed embodiment of the present invention.
Figure 13B:
Figure 14A:
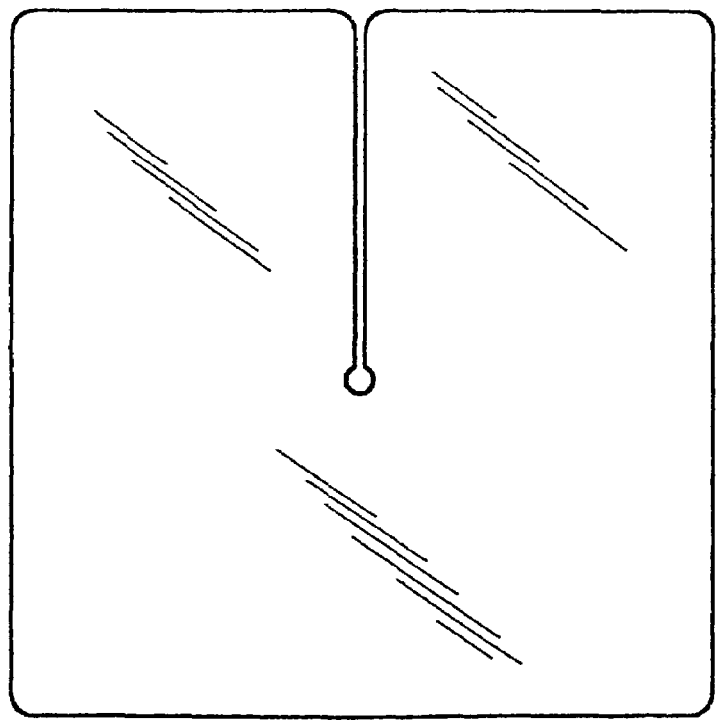
FIG. 14a is a top planar view of a scar-reduction resorbable barrier membrane in accordance with a twelfth pre-formed embodiment of the present invention.
Figure 14B:
Figures 17A, 17B:
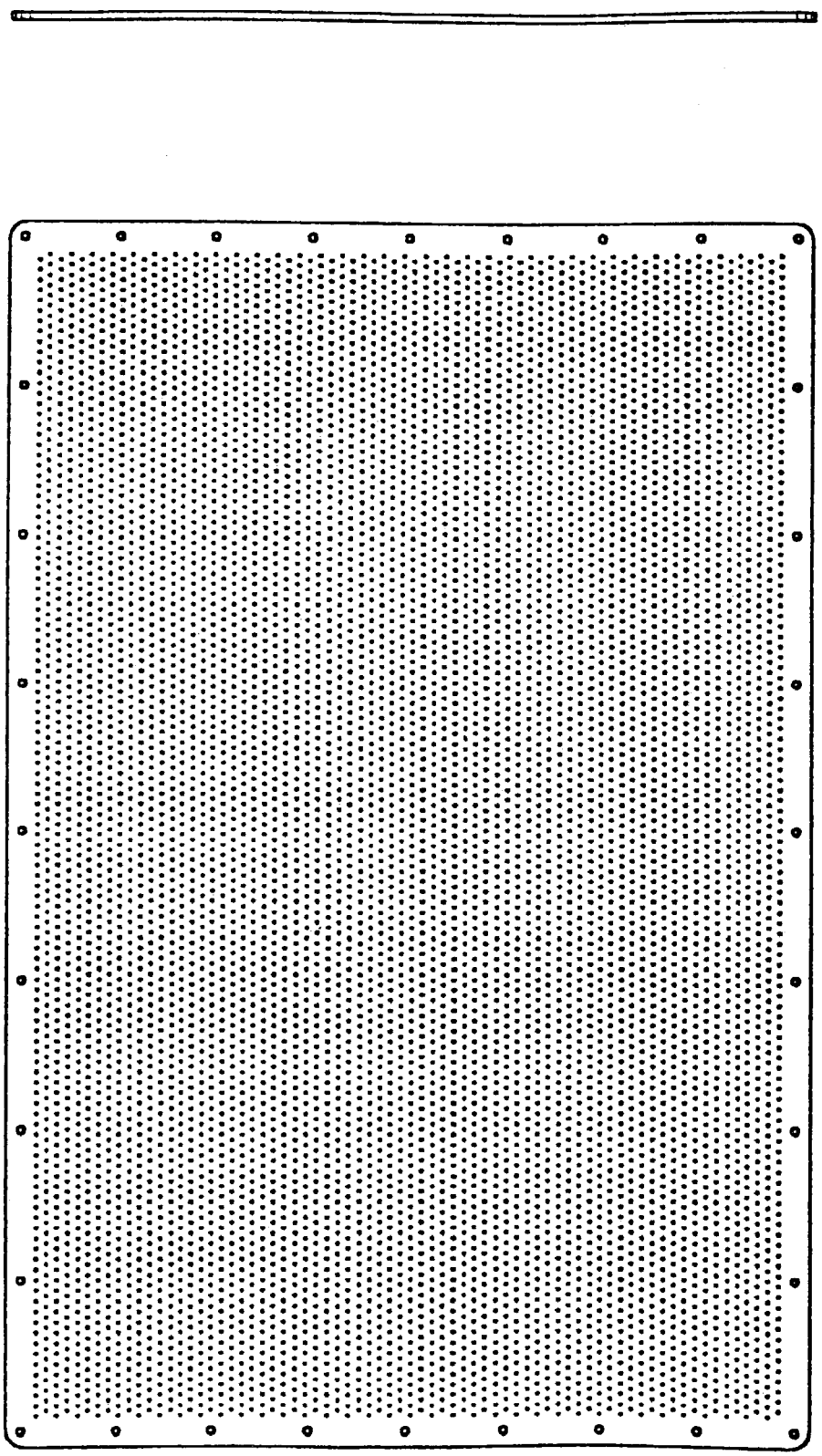

FIG. 2a illustrates a laminotomy procedure wherein a the two vertebrae 20 and 22 are separated and fixated using screws 24 and rods 26, and a portion of the lamina has been removed, leaving a window 28 (shown as a phantom rectangle) in the vertebrae 22. FIG. 2b is an enlarged view of the window 28 in the lamina of the vertebrae 22. The spinal chord 30 and an exiting nerve root 32 are thus exposed. In accordance with the present invention, the scar-reduction resorbable barrier membrane is applied to the dura of both the spinal chord 30 and the exiting nerve root 32, to thereby attenuate or eliminate the occurrence of post-operative scarring in the vicinity of the exiting nerve root 32. In a modified embodiment, a thicker bridging barrier membrane is applied to one or both of the vertebrae 20 and 22, to thereby bridge (i.e., tent) over and cover the window 28. This bridging barrier membrane may be non-porous, fluid permeable, cell permeable or vessel permeable in accordance with various embodiments, and preferably comprises a thickness between about 0.5 mm and 2.0 mm for preventing prolapse of adjacent muscle tissue into the foramen (i.e., the spinal lumen containing the spinal chord 30 and exiting nerve root 32). In accordance with various embodiments, the bridging barrier membrane may be used alone or in combination with the scar-reduction resorbable barrier membrane or, the scar-reduction resorbable barrier membrane may be used without the bridging barrier membrane.

In accordance with one aspect of the present invention, the scar-reduction resorbable barrier membrane can be heat bonded, such as with a bipolar electro-cautery device, ultrasonically welded, or similarly sealed directly to the dura of the spinal chord 30 and the exiting nerve root 32. Such a device can be used to heat the barrier membrane at various locations, such as at the edges and at points in the middle, at least above its glass transition temperature, and preferably above its softening point temperature. The glass transition temperature of the preferred material poly (L-lactide-co-D, L-lactide) is about 55° Celsius, while its softening point temperature is above 110° Celsius. The material is heated along with adjacent tissue such that the two components bond together at their interface. In another embodiment, the scar-reduction resorbable barrier membrane can be heat bonded or sealed directly to one or both of the vertebrae 20 and 22, or to muscle or other soft tissue, for example. In yet another embodiment, the scar-reduction resorbable barrier membrane can be heat bonded or sealed directly to itself in an application, for example, wherein the barrier membrane is wrapped around a structure and then heat joined to itself. Moreover, the technique of heat-sealing the barrier membrane material to itself or body tissue may be combined with another attachment method for enhanced anchoring. For example, the barrier membrane material may be temporarily affixed in position using two or more points of heat sealing (i.e., heat welding) using an electro-cautery device, and sutures, staples or glue can then be added to secure the barrier membrane into place.

Figure 18:
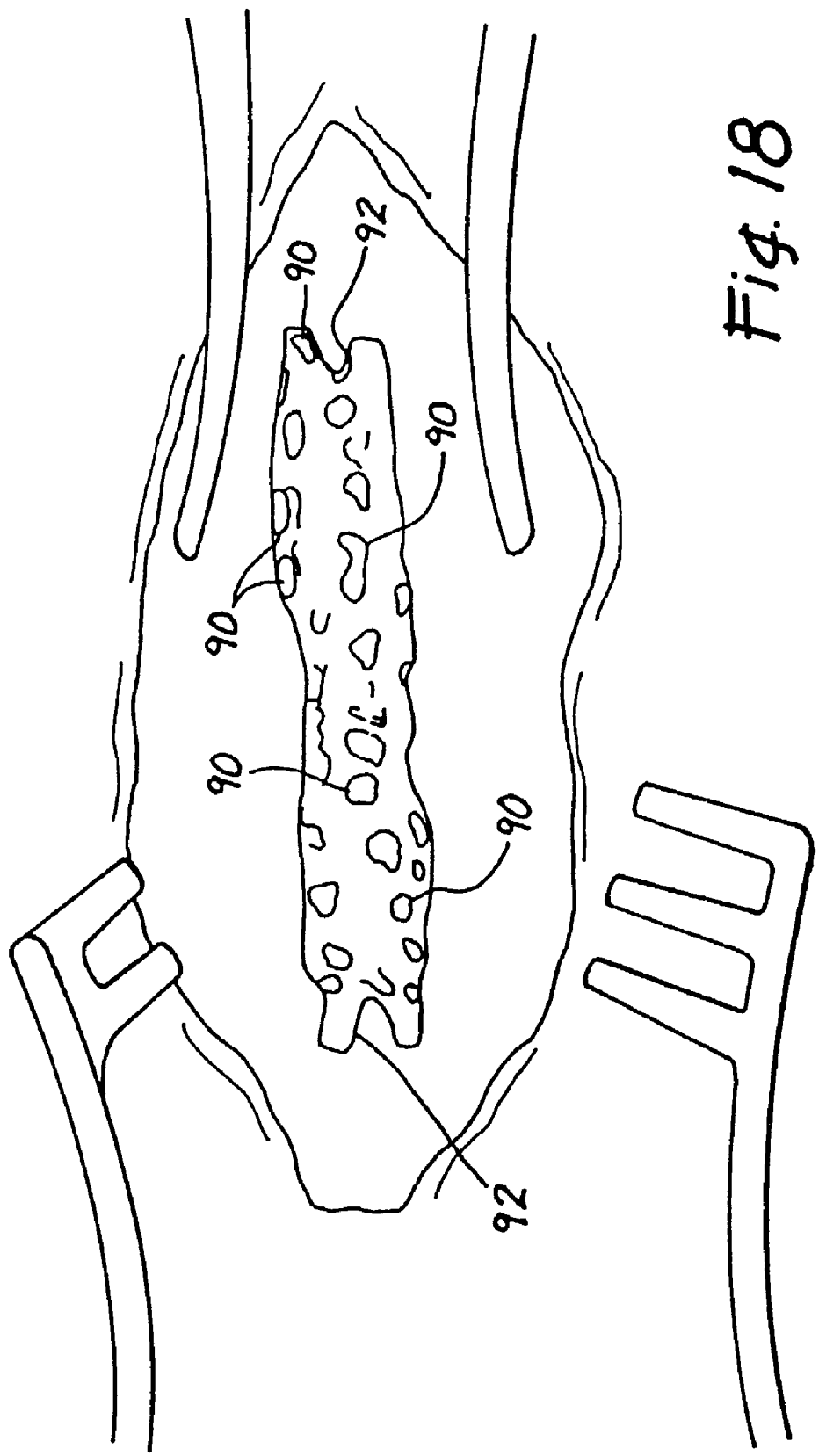
FIG. 18 is illustrates a scar-reduction resorbable barrier membrane of the present invention implanted on a rat spine, with two spinus processes of the spine protruding at opposing ends of the implant.

Turning to FIG. 3, a pre-formed scar-reduction resorbable barrier membrane 34 is formed with a first welding flange 36 and a second welding flange 38 thereon. A trunk portion 40 fits over the spinal chord 30, and a branch portion 42 fits over the exiting nerve root 32. The first welding flange 36 is formed by a first slit 44 and a second slit 46, and the second welding flange 38 is formed by a first slit 48 and a second slit 50. In application, the pre-formed scar-reduction resorbable barrier membrane 34 is placed over the spinal chord 30 and the exiting nerve root 32 and, subsequently, the first welding flange 36 and the second welding flange 38 are bent at least partially around the exiting nerve root. The rounded end 52 of the branch portion 42 fits onto a portion of the exiting nerve root 32 furthest away from the spinal chord 30. As presently embodied, the first welding flange 36 and the second welding flange are wrapped around, and preferably tucked beneath (i.e., behind) the exiting nerve root 32. In a preferred embodiment, the first welding flange 36 is then heat welded to the second welding flange 38. The flanges preferably are cut to wrap entirely around the exiting nerve root 32 and overlap one another. The first welding flange 36 maybe sutured to the second welding flange 38, alone or in addition with the heat welding step, to thereby secure the first welding flange 36 to the second welding flange 38. In another embodiment, neither heat welding nor suturing is used and the flanges are merely tucked partially or completely around the exiting nerve root 32 (depending on the dimensions of the root 32). When sutures are to be used, the pre-formed scar-reduction resorbable barrier membrane 34 may be pre-formed and packaged with optional suture apertures 60. The edges 64 and 66 are then preferably heat welded to the spinal chord 30. The two edges 68 and 70 form a third welding flange 72. A fourth welding flange 74 is formed by slits 76 and 78, and a fifth welding flange 80 is formed by slits 82 and 84. The welding flanges may be secured in manners similar to those discussed in connection with the welding flanges 36 and 38. Heat welds may further be secured along other edges and along the surface of the pre-formed scar-reduction resorbable barrier membrane 34, such as shown at 90 in FIG. 18. Moreover, notches may be formed on the barrier membranes of the present invention, such as, for example, at the ends 64 and 66 in modified-shape embodiments, for accommodating, for example, the spinal processes. Such exemplary notches are shown in FIG. 18 and 92.

FIG. 4 illustrates a scar-reduction resorbable barrier membrane for application to two exiting nerve roots 32 and 98 of the spinal chord in accordance with another pre-formed embodiment of the present invention. FIG. 5 illustrates a scar-reduction resorbable barrier membrane similar to that of FIG. 4 but adapted for application to four exiting nerve roots of the spinal chord in accordance with another pre-formed embodiment of the present invention. For example, the branch portion 100 is analogous in structure and operation to the branch portion 42 of the FIG. 3 embodiment, and the other branch portion 102 is constructed to accommodate the exiting nerve root 98. Similar elements are shown in FIG. 5 at 100a, 102a, 100b and 102c. The embodiments of FIGS. 6-17 illustrate other configurations for accommodating different anatomical structures. For example, the configurations of FIGS. 7, 10, 12, 14 and 15 are designed to be formed into, for example, a cone structure to fit around a base portion with a protrusion extending through the center of the barrier membrane. The illustrated embodiments of FIGS. 6-17 have suture perforations formed around their perimeters, and many are shown with cell and vessel permeable pores.

In accordance with the present invention, the pre-formed scar-reduction resorbable barrier membranes are preformed and sealed in sterilized packages for subsequent use by the surgeon. Since an objective of the scar-reduction resorbable barrier membranes of the present invention is to reduce sharp edges and surfaces, preformation of the barrier membranes is believed to help facilitate, albeit to a relatively small degree, rounding of the edges for less rubbing, tissue turbulence and inflammation. That is, the surfaces and any sharp edges of the scar-reduction resorbable barrier membranes are believed to be capable of slightly degrading over time in response to exposure of the barrier membranes to moisture in the air, to thereby form rounder edges. This is believed to be an extremely minor effect. Moreover, sterilization processes (E-beam or heat) on the cut, pre-packaged and/or packaged barrier membrane can further round any sharp edges, as can any initial heating to glass temperature of the pre-cut barrier membranes just before implanting. Moreover, the very thin scar-reduction resorbable barrier membranes of the present invention may be particularly susceptible to these phenomena, and, perhaps to a more noticeable extent, are susceptible to tearing or damage from handling, thus rendering the pre-forming of the scar-reduction resorbable barrier membranes beneficial for preserving the integrity thereof.

An embodiment of the scar-reduction resorbable barrier membrane has been tested in rat studies in comparison with several scar-tissue reduction barrier gels with favorable results. Specifically, the barrier membrane material of the present invention and the scar-tissue reduction gels were inserted around the spinal column of 52 male adult Sprague-Dawley rats, each weighing 400 plus grams. A posterior midline incision was made exposing the bony posterior elements from L4 to L7, and bilateral laminectomies were performed at the L5 and L6 level using surgical loupes. Following the laminectomies, the dura was retracted medially (to the left then to the right) using a microscope to expose the disc at L5/L6, and a bilateral controlled disc injury was performed using a 26 gauge needle. After hemostasis and irrigation, an anti-inflammatory agent was applied over both laminectomy sites.

The rats were divided and treated in five groups: 1) normal controls without surgery; 2) untreated, laminectomy only; 3) those to which 0.1 cc of high molecular weight hyaleronan (HA gel) was applied to the laminectomy site; 4) those to which 0.1 cc of Adcon-L scar-tissue reduction gel was applied to the laminectomy site; and 5) those that had an insertion of a barrier membrane of the present invention over the laminectomy site. The wounds were closed in a routine manner, and the survival period was three weeks.

After termination of each of the rats, the L5 segmental nerve roots were dissected free bilaterally using an anterior approach. The segmental nerve roots were excised including the portion of the nerve root within the foramen (1 cm in length). Additionally, the dura was exposed using an anterior approach. The dura from the caudal aspect of the body of L4 to the cephalad aspect of the body of L7 was removed (1.5 center in length) including all attached scar. The samples were analyzed biochemically by extracting the fat, then vacuum drying and determining the amount of total collagen and the percent of collagen from the hydroxyproline content. The amount of total collagen was expressed in milligrams and the percent of collagen was expressed as a percent of fat free dry weight.

Each treatment group was compared to both the normal controls and the operated but untreated controls using a Fisher's multiple comparisons paired t-test. Additionally, the treatment groups were compared using a one-way analysis of variance. In the untreated, laminotomy-only specimens, the total collagen increased more than two-fold in the dura (p value of 0.0009). In the untreated group, the percent collagen increased significantly in both the dura and nerve roots (p values of 0.001 and 0.005, respectively). Treatment with HA gel (p=0.010), Adcon-L (p=0.004), or the barrier membrane of the present invention (p=0.002) significantly reduced the amount of total collagen in the dura. Likewise, the same holds true for the percent collagen where the values are: HA gel (p=0.015), Adcon-L (p=0.041), and the barrier membrane of the present invention (p=0.011). There was a trend showing that the barrier membrane of the present invention decreased approximately 50% more both in total collagen and percent collagen compared to the HA gel and Adcon-L. In the nerve roots, the amount of total collagen and a percentage of collagen was not significantly changed by treatment with any of the HA gel, Adcon-L, or barrier membrane of the present invention.

These biochemical measurements of total and percent collagen enabled obtension of quantitative data on scar formation post laminotomy. Gross findings and biochemical analysis in the model demonstrated that the untreated laminotomy scar becomes adherent to the dorsum of the dura mater, a clearly undesirable outcome. Both a single application of HA gel or Adcon-L demonstrated a beneficial effect at the level of the dura. However, the half life of HA gel is less than 24 hours, and the Adcon-L is resorbed within approximately four weeks, which suggests that further long-term studies could be conducted. Additionally, Adcon-L has the potential to delay posterior wound healing, possibly leading to wound infections and/or wound dehiscences (few of the adverse events experienced by less than 1% of the study groups per product pamphlet). On the other hand, the barrier membrane of the present invention appears to wall off the overlying muscle, potentially protecting against cellular trafficking and vascular ingrowth, and does not appear to interfere with normal posterior wound healing. A possible improvement on the results obtained by using the barrier membrane of the present invention by itself may be obtained by using the barrier membrane in conjunction with an anti-inflammatory gel agent applied, for example, beneath the barrier membrane. Additionally, the scar-tissue reduction barrier membrane may be used in combination with a fixation device for stabilizing the bone defect, such as shown in connection with the two vertebrae 20 and 22 of FIG. 1.

Figure 19:
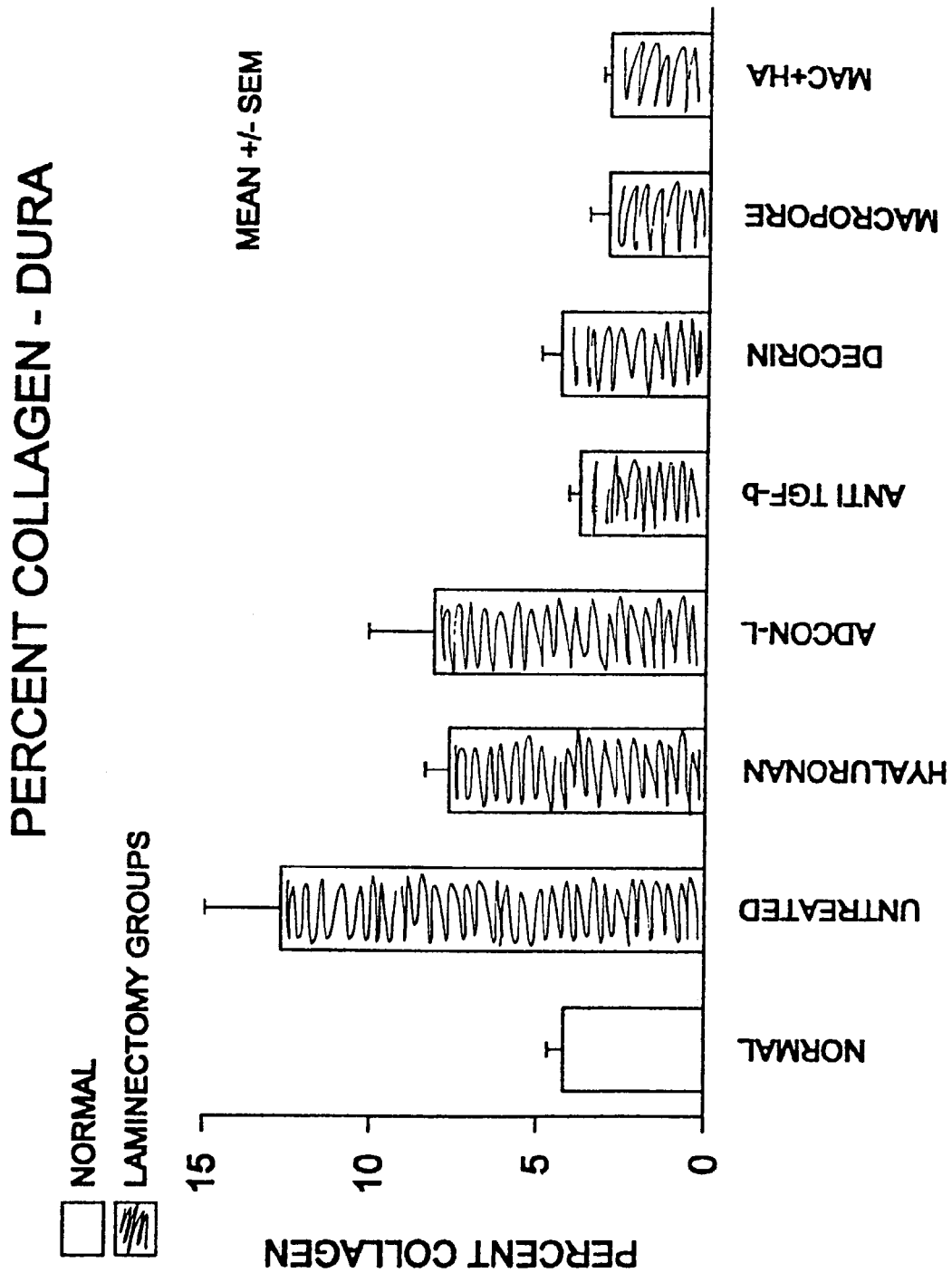
FIG. 19 is a bar graph showing the results of a study comparing the scar-reduction barrier membrane of the present invention against several other materials, and controls, indicating the percent collagen found in and around the dura following a surgical procedure after a period of about three weeks.

FIG. 19 illustrates a bar graph showing the percent collagen resulting from the aforementioned rat tests for various groups. The results for the barrier membrane of the present invention are labeled as Macropore, while the last result denoted MAC+HA is for the barrier membrane material of the present mention in conjunction with HA gel. The results indicate that there is a marked improvement over the HA gel or Adcon-L, and significant improvement in comparison with a tissue growth factor beta and a material known as Decorin.

Applicants hereby incorporate the entire disclosures of U.S. application Ser. No. 09/805,411, and all patents and other references cited therein, by reference.

While the foregoing is a complete description of the preferred embodiments of the invention, various alternatives, modifications, and equivalents may be used. Moreover, it will be apparent that certain other modifications may be practiced within the scope of the appended claims.

What is claimed is:

1. A method for governing bone growth, the method comprising providing a substantially planar barrier membrane of resorbable polymer base material having a bone-growing substantially-smooth side that comprises a bone-inductive factor and a non-bone growing substantially-smooth side, the substantially planar barrier membrane of resorbable polymer base material comprising a single layer of resorbable polymer base material between the bone-growing side and the non-bone growing side, the single layer of resorbable polymer base material having a substantially uniform composition, wherein a thickness of the single layer of resorbable polymer base material, measured between the bone-growing side and the non-bone growing side, is between about 10 microns and about 300 microns, wherein the single layer of resorbable polymer base material is non-porous, wherein the single layer of resorbable polymer base material consists essentially of a material selected from the group consisting of a poly-lactide polymer and a copolymer of two or more cyclic esters, and wherein the single layer of resorbable polymer base material is adapted to maintain a smooth-surfaced barrier between the bone growing side and the non-bone growing side, and is adapted to be resorbed into a mammalian body within a period of approximately 18 to 24 months from an initial implantation of the substantially planar barrier membrane of resorbable polymer base material into the mammalian body; and forming a spatial barrier with the substantially planar barrier membrane of resorbable polymer base material, the substantially planar barrier membrane of resorbable polymer base material separating a bone-growth area, which faces the bone-growing side having the bone-inductive factor, from a non-bone-growth area, which faces the non-bone growing side having a pre-implantation compositional characteristic different from a pre-implantation compositional characteristic of the bone growing side, wherein the compositional characteristic is defined by an amount or concentration of one or more of a tissue growth inhibitor or anti-tissue agent, an anti-bone agent or factor, an anti-angiogenic factor, a monoclonal or polyclonal antibody, an antibody fragment, a substance for cellular control, a chemotactic substance for influencing cell-migration, an inhibitory substance for influencing cell-migration, a mitogenic growth factor for influencing cell proliferation, a bone-inductive factor, a growth factor for influencing cell differentiation, and a factor which promotes angiogenesis.

2. The method of claim 1, wherein the resorbable polymer base material is about 70:30 poly (L-lactide-co-D,L-lactide).

3. The method of claim 1, wherein the spatial barrier is formed in a cavity of a bone of a patient.

4. The method as set forth in claim 1, wherein the characteristic of the non-bone growing side that is different from a characteristic of the bone-growing side comprises a concentration of bone morphogenic protein on the bone-growing side that is greater than a concentration of bone morphogenic protein on the non-bone growing side.

5. The method of claim 1, wherein the providing comprises providing a the non-bone growing substantially-smooth side substantially free of a bone inductive factor.

6. The method of claim 1, wherein the single layer of resorbable polymer base material is not fluid permeable.

7. The method of claim 1, further comprising administering at least one anti-tissue agent.

8. The method of claim 1, wherein the substantially planar barrier membrane of resorbable polymer base material is sealed in a sterile packaging.

9. The method of claim 7, wherein the at least one anti-tissue agent comprises at least one anti-bone factor to inhibit bone tissue growth in the non-bone-growth area.

10. The method of claim 9, wherein the at least one anti-bone factor is administered into the non-bone-growth area.

11. The method of claim 1, wherein the governing of bone growth is in a spinal canal and wherein the forming of a spatial barrier comprises positioning the substantially planar barrier membrane of resorbable polymer base material to form a spatial barrier between a bone-growth area, which faces the bone-growing side, and the spinal canal, which faces the non-bone growing side having a characteristic different from a characteristic of the bone-growing side.

12. The method as set forth in claim 11, wherein the characteristic of the non-bone growing side that is different from a characteristic of the bone-growing side comprises a concentration of bone morphogenic protein of the bone-growing side that is greater than a concentration of bone morphogenic protein of the non-bone growing side.

13. The method of claim 11, wherein implant comprises a promoter of cell growth disposed substantially only on the bone growing side of the implant.

14. The method of claim 11, wherein implant comprises an inhibitor of cell growth disposed substantially only on the non-bone growing side of the implant.

15. The method of claim 14, wherein the inhibitor of cell growth includes one or more of anti-angiogenic factors, monoclonal or polyclonal antibodies, and combinations thereof.

16. The method of claim 14, wherein the inhibitor of cell growth is effective against members of the transforming growth factor (TGF)-beta superfamily.

17. The method of claim 11, wherein the implant comprises:

a promoter of cell growth disposed substantially only on the bone-growing side of the implant; and an inhibitor of cell growth disposed substantially only on the non-bone growing side of the implant.

18. The method of claim 1, wherein:
the governing of bone growth comprises governing bone growth in a cavity in a bone;
the forming of a spatial barrier comprises inserting the substantially planar barrier membrane of resorbable polymer base material into the cavity so that the at least one resorbable barrier membrane defines the bone-growth area and the non-bone-growth area, each of the bone-growth area and the non-bone-growth area being disposed on opposite sides of the substantially planar barrier membrane of resorbable polymer base material before the substantially planar barrier membrane of resorbable polymer base material is resorbed; and
the method farther comprises administering at least one tissue growth inhibitor to inhibit tissue growth in a vicinity only of the non-bone-growth area, wherein the substantially planar barrier membrane of resorbable polymer base material governs bone growth by reducing tissue-growth in the non-bone-growth area.

19. The method of claim 18, further comprising administering a bone morphogenic protein to the bone-growth area to enhance bone growth in the bone-growth area.

20. The method of claim 19, wherein the bone morphogenic protein is provided on the surface of the substantially planar barrier membrane of resorbable polymer base material facing the bone-growth area.

21. The method of claim 18, further comprising administering at least one anti-bone factor to inhibit bone tissue growth in the non-bone-growth area.

22. The method of claim 21, wherein the at least one anti-bone factor is provided only on a surface of the substantially planar barrier membrane of resorbable polymer base material facing the non-bone-growth area.

23. The method of claim 18, wherein the substantially planar barrier membrane of resorbable polymer base material is inserted adjacent to the spinal meninges to reduce bone growth into the spinal canal of the patient.

24. The method of claim 18, wherein the substantially planar barrier membrane of resorbable polymer base material comprises a poly-lactide polymer and a copolymer of at least two lactides.

25. The method of claim 18, wherein the substantially planar barrier membrane of resorbable polymer base material is impermeable to fluid.

26. The method of claim 18, further comprising attaching the substantially planar barrier membrane of resorbable polymer base material to an anatomical structure to provide a fixed border between the bone-growth area and the non-bone-growth area.

27. The method of claim 26, wherein the substantially planar barrier membrane of resorbable polymer base material is attached to a muscle.

28. The method of claim 26, wherein the substantially planar barrier membrane of resorbable polymer base material is attached to bone.

29. The method of claim 18, wherein the substantially planar barrier membrane of resorbable polymer base material is inserted into the cavity to prevent movement of cells from the bone-growth area to the non-bone-growth area.

30. The method of claim 18, further comprising forming the substantially planar barrier membrane of resorbable polymer base material with a cellular control substance at least one predetermined location on the substantially planar barrier membrane of resorbable polymer base material.

31. The method of claim 30, wherein the substantially planar barrier membrane of resorbable polymer base material is formed with an inhibitor of cell growth disposed substantially only on one side of the substantially planar barrier membrane of resorbable polymer base material.

32. The method of claim 30, wherein the substantially planar barrier membrane of resorbable polymer base material is formed with a promoter of cell growth disposed substantially only on one side of the substantially planar barrier membrane of resorbable polymer base material.

33. The method of claim 18, wherein the substantially planar barrier membrane of resorbable polymer base material is resorbed at a rate, and the method further comprises controlling the rate at which the substantially planar barrier membrane of resorbable polymer base material is resorbed.

34. The method of claim 18, wherein the substantially planar barrier membrane of resorbable polymer base material comprises a copolymer of epsilon-caprolactone and a lactide.

35. A method for governing bone growth, the method comprising providing a substantially planar barrier membrane of resorbable polymer base material having a bone-growing substantially-smooth side and a non-bone growing substantially-smooth side, the substantially planar barrier membrane of resorbable polymer base material comprising a single layer of resorbable polymer base material between the bone-growing side and the non-bone growing side, the single layer of resorbable polymer base material having a substantially uniform composition, wherein a thickness of the single layer of resorbable polymer base material, measured between the bone-growing side and the non-bone growing side, is about 100 microns, wherein the single layer of resorbable polymer base material is non-porous, wherein the single layer of resorbable polymer base material consists essentially of a material selected from the group consisting of a poly-lactide polymer and a copolymer of two or more cyclic esters, and wherein the single layer of resorbable polymer base material is adapted to maintain a smooth-surfaced barrier between the bone growing side and the non-bone growing side, and is adapted to be resorbed into a mammalian body within a period of approximately 18 to 24 months from an initial implantation of the substantially planar barrier membrane of resorbable polymer base material into the mammalian body; and forming a spatial barrier with the substantially planar barrier membrane of resorbable polymer base material, the substantially planar barrier membrane of resorbable polymer base material separating a bone-growth area, which faces the bone-growing side having a bone inductive factor, from a non-bone-growth area, which faces the non-bone growing side having a pre-implantation compositional characteristic different from a pre-implantation compositional characteristic of the bone growing side, wherein the compositional characteristic is defined by an amount or concentration of one or more of a tissue growth inhibitor or anti-tissue agent, an anti-bone agent or factor, an anti-angiogenic factor, a monoclonal or polyclonal antibody, an antibody fragment, a substance for cellular control, a chemotactic substance for influencing cell-migration, an inhibitory substance for influencing cell-migration, a mitogenic growth factor for influencing cell proliferation, a bone-inductive factor, a growth factor for influencing cell differentiation, and a factor which promotes angiogenesis.

36. A method for governing bone growth, the method comprising providing a substantially planar barrier membrane of resorbable polymer base material having a bone-growing substantially-smooth side and a non-bone growing substantially-smooth side, the substantially planar barrier membrane of resorbable polymer base material comprising a single layer of resorbable polymer base material between the bone-growing side and the non-bone growing side, the single layer of resorbable polymer base material having a substantially uniform composition, wherein a thickness of the single layer of resorbable polymer base material, measured between the bone-growing side and the non-bone growing side, is about 200 microns, wherein the single layer of resorbable polymer base material is non-porous, wherein the single layer of resorbable polymer base material consists essentially of a material selected from the group consisting of a poly-lactide polymer and a copolymer of two or more cyclic esters, and wherein the single layer of resorbable polymer base material is adapted to maintain a smooth-surfaced barrier between the bone growing side and the non-bone growing side, and is adapted to be resorbed into a mammalian body within a period of approximately 18 to 24 months from an initial implantation of the substantially planar barrier membrane of resorbable polymer base material into the mammalian body; and forming a spatial barrier with the substantially planar barrier membrane of resorbable polymer base material, the substantially planar barrier membrane of resorbable polymer base material separating a bone-growth area, which faces the bone-growing side having a bone inductive factor, from a non-bone-growth area, which faces the non-bone growing side having a pre-implantation compositional characteristic, which is defined by an amount or concentration of one or more of a tissue growth inhibitor or anti-tissue agent, an anti-bone agent or factor, an anti-angiogenic factor, a monoclonal or polyclonal antibody, an antibody fragment, a substance for cellular control, a chemotactic substance for influencing cell-migration, an inhibitory substance for influencing cell-migration, a mitogenic growth factor for influencing cell proliferation, a bone-inductive factor, a growth factor for influencing cell differentiation, and a factor which promotes angiogenesis, and which is different from a pre-implantation compositional characteristic of the bone growing side.

37. A method for governing bone growth, the method comprising providing a substantially planar barrier membrane of resorbable polymer base material having a bone-growing substantially-smooth side and a non-bone growing substantially-smooth side, the substantially planar barrier membrane of resorbable polymer base material comprising a single layer of resorbable polymer base material between the bone-growing side and the non-bone growing side, the single layer of resorbable polymer base material having a substantially uniform composition, wherein a thickness of the single layer of resorbable polymer base material, measured between the bone-growing side and the non-bone growing side, is between about 10 microns and about 300 microns, wherein the single layer of resorbable polymer base material is non-porous, wherein the single layer of resorbable polymer base material consists essentially of a material selected from the group consisting of a poly-lactide polymer and a copolymer of two or more cyclic esters, and wherein the single layer of resorbable polymer base material is adapted to maintain a smooth-surfaced barrier between the bone growing side and the non-bone growing side, and is adapted to be resorbed into a mammalian body within a period of approximately 18 to 24 months from an initial implantation of the substantially planar barrier membrane of resorbable polymer base material into the mammalian body; and forming a spatial barrier with the substantially planar barrier membrane of resorbable polymer base material, the substantially planar barrier membrane of resorbable polymer base material separating a bone-growth area, which faces the bone-growing side having a bone inductive factor, from a non-bone-growth area, which faces the non-bone growing side having a pre-implantation compositional characteristic, which is defined by an amount or concentration of one or more of a tissue growth inhibitor or anti-tissue agent, an anti-bone agent or factor, an anti-angiogenic factor, a monoclonal or polyclonal antibody, an antibody fragment, a substance for cellular control, a chemotactic substance for influencing cell-migration, an inhibitory substance for influencing cell-migration, a mitogenic growth factor for influencing cell proliferation, a bone-inductive factor, a growth factor for influencing cell differentiation, and a factor which promotes angiogenesis, and which is different from a pre-implantation compositional characteristic of the bone growing side, wherein the substantially planar barrier membrane or resorbable polymer base material is impregnated with at least one of an anti-bone agent, a chemotactic substance for influencing cell-migration, an inhibitory substance for influencing cell-migration, a mitogenic growth factor for influencing cell proliferation, a growth factor for influencing cell differentiation, and factors which promote angiogenesis.

38. A method for governing bone growth, the method comprising providing a substantially planar baffler membrane of resorbable polymer base material having a bone-growing substantially-smooth side and a non-bone growing substantially-smooth side, the substantially planar barrier membrane of resorbable polymer base material comprising a single layer of resorbable polymer base material between the bone-growing side and the non-bone growing side, the single layer of resorbable polymer base material having a substantially uniform composition, wherein a thickness of the single layer of resorbable polymer base material, measured between the bone-growing side and the non-bone growing side, is less than 300 microns, wherein the single layer of resorbable polymer base material is non-porous, wherein the single layer of resorbable polymer base material consists essentially of a material selected from the group consisting of a poly-lactide polymer and a copolymer of two or more cyclic esters, and wherein the single layer of resorbable polymer base material is adapted to maintain a smooth-surfaced barrier between the bone growing side and the non-bone growing side, and is adapted to be resorbed into a mammalian body within a period of approximately 18 to 24 months from an initial implantation of the substantially planar barrier membrane of resorbable polymer base material into the mammalian body; and forming a spatial barrier with the substantially planar barrier membrane of resorbable polymer base material, the substantially planar baffler membrane of resorbable polymer base material separating a bone-growth area, which faces the bone-growing side having a bone inductive factor, from a non-bone-growth area, which faces the non-bone growing side having a pre-implantation compositional characteristic different from a pre-implantation compositional characteristic of the bone growing side, wherein the compositional characteristic is defined by an amount or concentration of one or more of a tissue growth inhibitor or anti-tissue agent, an anti-bone agent or factor, an anti-angiogenic factor, a monoclonal or polyclonal antibody, an antibody fragment, a substance for cellular control, a chemotactic substance for influencing cell-migration, an inhibitory substance for influencing cell-migration, a mitogenic growth factor for influencing cell proliferation, a bone-inductive factor, a growth factor for influencing cell differentiation, and a factor which promotes angiogenesis, whereby the substantially planar barrier membrane of resorbable polymer base material has a thickness less than 300 microns and is substantially non-porous.

39. A method for governing bone growth, the method comprising providing a substantially planar barrier membrane of resorbable polymer base material having a bone-growing substantially-smooth side and a non-bone growing substantially-smooth side, the substantially planar barrier membrane of resorbable polymer base material comprising a single layer of resorbable polymer base material between the bone-growing side and the non-bone growing side, the single layer of resorbable polymer base material having a substantially uniform composition, wherein a thickness of the single layer of resorbable polymer base material, measured between the bone-growing side and the non-bone growing side, is between about 10 microns and about 300 microns, wherein the single layer of resorbable polymer base material is non-porous, wherein the single layer of resorbable polymer base material consists essentially of a material selected from the group consisting of a poly-lactide polymer and a copolymer of two or more cyclic esters, and wherein the single layer of resorbable polymer base material is adapted to maintain a smooth-surfaced barrier between the bone growing side and the non-bone growing side, and is adapted to be resorbed into a mammalian body within a period of approximately 18 to 24 months from an initial implantation of the substantially planar barrier membrane of resorbable polymer base material into the mammalian body; and forming a spatial barrier with the substantially planar barrier membrane of resorbable polymer base material, the substantially planar barrier membrane of resorbable polymer base material separating a bone-growth area, which faces the bone-growing side having a bone inductive factor, from a non-bone-growth area, which faces the non-bone growing side having a pre-implantation compositional characteristic, which is defined by an amount or concentration of one or more of a tissue growth inhibitor or anti-tissue agent, an anti-bone agent or factor, an anti-angiogenic factor, a monoclonal or polyclonal antibody, an antibody fragment, a substance for cellular control, a chemotactic substance for influencing cell-migration, an inhibitory substance for influencing cell-migration, a mitogenic growth factor for influencing cell proliferation, a bone-inductive factor, a growth factor for influencing cell differentiation, and a factor which promotes angiogenesis, and which is different from a pre-implantation compositional characteristic of the bone growing side, wherein the at least one anti-tissue agent comprises at least one anti-bone factor to inhibit bone tissue growth in the non-bone-growth area, and wherein the at least one anti-bone factor is administered to a surface of the substantially planar barrier membrane of resorbable polymer base material that is positioned to face the non-bone-growth area.

40. A method for governing bone growth, the method comprising providing a substantially planar barrier membrane of resorbable polymer base material having a bone-growing substantially-smooth side and a non-bone growing substantially-smooth side, the substantially planar barrier membrane of resorbable polymer base material comprising a single layer of resorbable polymer base material between the bone-growing side and the non-bone growing side, the single layer of resorbable polymer base material having a substantially uniform composition, wherein a thickness of the single layer of resorbable polymer base material, measured between the bone-growing side and the non-bone growing side, is between about 10 microns and about 300 microns, wherein the single layer of resorbable polymer base material is non-porous, wherein the single layer of resorbable polymer base material consists essentially of a material selected from the group consisting of a poly-lactide polymer and a copolymer of two or more cyclic esters, and wherein the single layer of resorbable polymer base material is adapted to maintain a smooth-surfaced barrier between the bone growing side and the non-bone growing side, and is adapted to be resorbed into a mammalian body within a period of approximately 18 to 24 months from an initial implantation of the substantially planar barrier membrane of resorbable polymer base material into the mammalian body; and forming a spatial barrier with the substantially planar barrier membrane of resorbable polymer base material, the substantially planar barrier membrane of resorbable polymer base material separating a bone-growth area, which faces the bone-growing side having a bone inductive factor, from a non-bone-growth area, which faces the non-bone growing side having a pre-implantation compositional characteristic different from a pre-implantation compositional characteristic of the bone growing side, wherein the providing comprises providing the bone-growing substantially-smooth side with a bone inductive factor and the non-bone growing substantially-smooth side substantially free of the bone inductive factor, wherein the compositional characteristic is defined by an amount or concentration of one or more of a tissue growth inhibitor or anti-tissue agent, an anti-bone agent or factor, an anti-angiogenic factor, a monoclonal or polyclonal antibody, an antibody fragment, a substance for cellular control, a chemotactic substance for influencing cell-migration, an inhibitory substance for influencing cell-migration, a mitogenic growth factor for influencing cell proliferation, a bone-inductive factor, a growth factor for influencing cell differentiation, and a factor which promotes angiogenesis.

41. A method for governing bone growth, the method comprising providing a substantially planar barrier membrane of resorbable polymer base material having a bone-growing substantially-smooth side and a non-bone growing substantially-smooth side, the substantially planar barrier membrane of resorbable polymer base material comprising a single layer of resorbable polymer base material between the bone-growing side and the non-bone growing side, the single layer of resorbable polymer base material having a substantially uniform composition, wherein a thickness of the single layer of resorbable polymer base material, measured between the bone-growing side and the non-bone growing side, is between about 10 microns and about 300 microns, wherein the single layer of resorbable polymer base material is non-porous, wherein the single layer of resorbable polymer base material consists essentially of a material selected from the group consisting of a poly-lactide polymer and a copolymer of two or more cyclic esters, and wherein the single layer of resorbable polymer base material is adapted to maintain a smooth-surfaced barrier between the bone growing side and the non-bone growing side, and is adapted to be resorbed into a mammalian body within a period of approximately 18 to 24 months from an initial implantation of the substantially planar barrier membrane of resorbable polymer base material into the mammalian body; and forming a spatial barrier with the substantially planar barrier membrane of resorbable polymer base material, the substantially planar barrier membrane of resorbable polymer base material separating a bone-growth area, which faces the bone-growing side having a bone inductive factor, from a non-bone-growth area, which faces the non-bone growing side having a pre-implantation compositional characteristic different from a pre-implantation compositional characteristic of the bone growing side, wherein the substantially planar barrier membrane of resorbable polymer base material comprises at least one tissue growth inhibitor and the compositional characteristic is defined by an amount or concentration of one or more of a tissue growth inhibitor or anti-tissue agent, an anti-bone agent or factor, an anti-angiogenic factor, a monoclonal or polyclonal antibody, an antibody fragment, a substance for cellular control, a chemotactic substance for influencing cell-migration, an inhibitory substance for influencing cell-migration, a mitogenic growth factor for influencing cell proliferation, a bone-inductive factor, a growth factor for influencing cell differentiation, and a factor which promotes angiogenesis.

42. The method of claim 41, wherein the substantially planar barrier membrane of resorbable polymer base material is impregnated with at least one tissue growth inhibitor.

43. The method of claim 42, wherein the at least one tissue growth inhibitor is an anti-bone factor.

44. The method of claim 43, wherein the anti-bone factor includes one or more of anti-angiogenic factors, monoclonal or polyclonal antibodies, and combinations thereof.

45. The method of claim 43, wherein the anti-bone factor is effective against members of the transforming growth factor (TGF)-beta superfamily.

46. A method for governing bone growth in a bone cavity, comprising:
    providing a smooth-surfaced resorbable polymer barrier membrane-which is about 10 to 300 microns thick and adapted to be resorbed in about 18 to 24 months and which has a bone-growing side with a bone inductive factor and a non-bone-growing side substantially free of the bone inductive factor; and
    inserting the resorbable barrier membrane into a bone cavity of a patient so that the resorbable barrier membrane defines a bone-growth area and a non-bone-growth area, each of the bone-growth area and the non-bone-growth area being disposed on opposite sides of the resorbable barrier membrane before the resorbable barrier membrane is resorbed, wherein the resorbable barrier membrane comprises an agent that governs bone growth by limiting bone-growth in the non-bone-growth area relative to a growth of bone in the bone-growth area.

47. The method of claim 46, further comprising administering at least one anti-bone factor to inhibit bone tissue growth in the non-bone-growth area.

48. The method of claim 47, wherein the at least one anti-bone factor is provided on a surface of the resorbable barrier membrane that faces the non-bone-growth area.

49. The method of claim 47, wherein the resorbable barrier membrane is inserted adjacent to the spinal meninges to reduce bone growth into the spinal canal of the patient.

50. The method of claim 47, wherein the resorbable barrier membrane comprises a poly-lactide polymer and a copolymer of at least two poly-lactides.

51. The method of claim 47, wherein the resorbable barrier membrane is impermeable to fluid.

52. The method of claim 46, wherein the implant comprises a promoter of cell growth disposed substantially only on the bone growing side of the implant.

53. The method of claim 46, wherein the implant comprises an inhibitor of cell growth disposed substantially only on the non-bone growing side of the implant.

54. The method of claim 53, wherein the inhibitor of cell growth includes one or more of anti-angiogenic factors, monoclonal or polyclonal antibodies, and combinations thereof.

55. The method of claim 53, wherein the inhibitor of cell growth is effective against members of the transforming growth factor (TGF)-beta superfamily.

56. The method of claim 46, wherein the implant comprises:
    a promoter of cell growth disposed substantially only on the bone-growing side of the implant; and
    an inhibitor of cell growth disposed substantially only on the non-bone growing side of the implant.

57. A method for governing bone growth, the method comprising providing a substantially planar barrier membrane of resorbable polymer base material having a bone-growing substantially-smooth side and a non-bone growing substantially-smooth side, the substantially planar barrier membrane of resorbable polymer base material comprising a single layer of resorbable polymer base material between the bone-growing side and the non-bone growing side, the single layer of resorbable polymer base material having a substantially uniform composition, wherein a thickness of the single layer of resorbable polymer base material, measured between the bone-growing side and the non-bone growing side, is between about 10 microns and about 300 microns, wherein the single layer of resorbable polymer base material is non-porous, wherein the single layer of resorbable polymer base material consists essentially of a material selected from the group consisting of a poly-lactide polymer and a copolymer of two or more cyclic esters, and wherein the single layer of resorbable polymer base material is adapted to maintain a smooth-surfaced barrier between the bone growing side and the non-bone growing side, and is adapted to be resorbed into a mammalian body within a period of approximately 18 to 24 months from an initial implantation of the substantially planar barrier membrane of resorbable polymer base material into the mammalian body; and forming a spatial barrier with the substantially planar barrier membrane of resorbable polymer base material, the substantially planar barrier membrane of resorbable polymer base material separating a bone-growth area, which faces the bone-growing side having a bone inductive factor, from a non-bone-growth area, which faces the non-bone growing side having a pre-implantation compositional characteristic, which is defined by an amount or concentration of one or more of a tissue growth inhibitor or anti-tissue agent, an anti-bone agent or factor, an anti-angiogenic factor, a monoclonal or polyclonal antibody, an antibody fragment, a substance for cellular control, a chemotactic substance for influencing cell-migration, an inhibitory substance for influencing cell-migration, a mitogenic growth factor for influencing cell proliferation, a bone-inductive factor, a growth factor for influencing cell differentiation, and a factor which promotes angiogenesis, and which is different from a pre-implantation compositional characteristic of the bone growing side, wherein the providing comprises providing a non-bone growing substantially-smooth side that is substantially free of a bone inductive factor, and wherein the providing further comprises providing the non-bone growing substantially-smooth side with a tissue growth inhibitor.

58. A method for governing bone growth, the method comprising providing a substantially planar barrier membrane of resorbable polymer base material having a bone-growing substantially-smooth side and a non-bone growing substantially-smooth side, the substantially planar barrier membrane of resorbable polymer base material comprising a single layer of resorbable polymer base material between the bone-growing side and the non-bone growing side, the single layer of resorbable polymer base material having a substantially uniform composition, wherein a thickness of the single layer of resorbable polymer base material, measured between the bone-growing side and the non-bone growing side, is between about 10 microns and about 300 microns, wherein the single layer of resorbable polymer base material is non-porous, wherein the single layer of resorbable polymer base material consists essentially of a material selected from the group consisting of a poly-lactide polymer and a copolymer of two or more cyclic esters, and wherein the single layer of resorbable polymer base material is adapted to maintain a smooth-surfaced barrier between the bone growing side and the non-bone growing side, and is adapted to be resorbed into a mammalian body within a period of approximately 18 to 24 months from an initial implantation of the substantially planar barrier membrane of resorbable polymer base material into the mammalian body; and forming a spatial barrier with the substantially planar barrier membrane of resorbable polymer base material, the substantially planar barrier membrane of resorbable polymer base material separating a bone-growth area, which faces the bone-growing side having a bone inductive factor, from a non-bone-growth area, which faces the non-bone growing side having a pre-implantation compositional characteristic different from a pre-implantation compositional characteristic of the bone growing side, wherein the compositional characteristic is defined by an amount or concentration of one or more of a tissue growth inhibitor or anti-tissue agent, an anti-bone agent or factor, an anti-angiogenic factor, a monoclonal or polyclonal antibody, an antibody fragment, a substance for cellular control, a chemotactic substance for influencing cell-migration, an inhibitory substance for influencing cell-migration, a mitogenic growth factor for influencing cell proliferation, a bone-inductive factor, a growth factor for influencing cell differentiation, and a factor which promotes angiogenesis, and wherein the providing comprises providing a non-bone growing substantially-smooth side that is substantially free of a bone inductive factor, and wherein the providing further comprises providing the non-bone growing substantially-smooth side with an anti-bone factor.

59. A method for governing bone growth, the method comprising providing a substantially planar barrier membrane of resorbable polymer base material having a bone-growing substantially-smooth side and a non-bone growing substantially-smooth side, the substantially planar barrier membrane of resorbable polymer base material comprising a single layer of resorbable polymer base material between the bone-growing side and the non-bone growing side, the single layer of resorbable polymer base material having a substantially uniform composition, wherein a thickness of the single layer of resorbable polymer base material, measured between the bone-growing side and the non-bone growing side, is between about 10 microns and about 300 microns, wherein the single layer of resorbable polymer base material is non-porous, wherein the single layer of resorbable polymer base material consists essentially of a material selected from the group consisting of a poly-lactide polymer and a copolymer of two or more cyclic esters, and wherein the single layer of resorbable polymer base material is adapted to maintain a smooth-surfaced barrier between the bone growing side and the non-bone growing side, and is adapted to be resorbed into a mammalian body within a period of approximately 18 to 24 months from an initial implantation of the substantially planar barrier membrane of resorbable polymer base material into the mammalian body; and forming a spatial barrier with the substantially planar barrier membrane of resorbable polymer base material, the substantially planar barrier membrane of resorbable polymer base material separating a bone-growth area, which faces the bone-growing side having a bone inductive factor, from a non-bone-growth area, which faces the non-bone growing side having a pre-implantation compositional characteristic, which is defined by an amount or concentration of one or more of a tissue growth inhibitor or anti-tissue agent, an anti-bone agent or factor, an anti-angiogenic factor, a monoclonal or polyclonal antibody, an antibody fragment, a substance for cellular control, a chemotactic substance for influencing cell-migration, an inhibitory substance for influencing cell-migration, a mitogenic growth factor for influencing cell proliferation, a bone-inductive factor, a growth factor for influencing cell differentiation, and a factor which promotes angiogenesis, and which is different from a pre-implantation compositional characteristic of the bone growing side, wherein the providing comprises providing the substantially planar barrier membrane of resorbable polymer base material having a bone-growing substantially-smooth side and a non-bone growing substantially-smooth side, the non-bone growing substantially-smooth side comprising at least one anti-bone factor.

* * * * *